United States Patent
Kanai

(10) Patent No.: US 10,306,110 B2
(45) Date of Patent: May 28, 2019

(54) MEASURING DEVICE AND PRINTING APPARATUS

(71) Applicant: Seiko Epson Corporation, Tokyo (JP)

(72) Inventor: Masashi Kanai, Azumino (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 15/333,340

(22) Filed: Oct. 25, 2016

(65) Prior Publication Data

US 2017/0126933 A1 May 4, 2017

(30) Foreign Application Priority Data

Oct. 29, 2015 (JP) .................. 2015-213409

(51) Int. Cl.
*G01J 3/02* (2006.01)
*G01J 3/10* (2006.01)
*G01J 3/12* (2006.01)
*G01J 3/26* (2006.01)
*G01J 3/28* (2006.01)
*G01J 3/50* (2006.01)
*G01J 3/51* (2006.01)
*G01J 3/52* (2006.01)
*H04N 1/00* (2006.01)
*H04N 1/60* (2006.01)
*G01N 21/25* (2006.01)

(52) U.S. Cl.
CPC ............ *H04N 1/6097* (2013.01); *G01J 3/027* (2013.01); *G01J 3/0291* (2013.01); *G01J 3/10* (2013.01); *G01J 3/12* (2013.01); *G01J 3/26* (2013.01); *G01J 3/50* (2013.01); *G01J 3/51* (2013.01); *G01J 3/524* (2013.01); *G01N 21/255* (2013.01); *H04N 1/00023* (2013.01); *H04N 1/00034* (2013.01); *H04N 1/00045* (2013.01); *H04N 1/00058* (2013.01); *H04N 1/6044* (2013.01); *G01J 3/28* (2013.01); *G01J 2003/102* (2013.01); *G01J 2003/1226* (2013.01); *G01N 2201/061* (2013.01)

(58) Field of Classification Search
None
See application file for complete search history.

(56) References Cited

U.S. PATENT DOCUMENTS

| | | | | |
|---|---|---|---|---|
| 5,050,991 A | * | 9/1991 | Welch ........................ | G01J 3/42 356/326 |
| 5,642,189 A | * | 6/1997 | Alguard ................ | G01J 3/0259 250/461.1 |
| 5,642,192 A | * | 6/1997 | Gordon ..................... | G01J 3/10 356/328 |
| 5,854,680 A | * | 12/1998 | Rakitsch ................... | G01J 3/02 356/406 |

(Continued)

FOREIGN PATENT DOCUMENTS

JP 2013-117632 A 6/2013

*Primary Examiner* — Anh-Vinh T Nguyen
(74) *Attorney, Agent, or Firm* — Harness, Dickey & Pierce, P.L.C.

(57) ABSTRACT

A printer includes a spectrometer which is relatively movable between media having a front surface of the media and a rear surface of the media which is opposite to the first surface and a platen which holds the second surface of the media. The platen includes a plurality of light transmitting units transmitting light.

17 Claims, 16 Drawing Sheets

(56) References Cited

U.S. PATENT DOCUMENTS

| | | | | |
|---|---|---|---|---|
| 6,249,348 B1* | 6/2001 | Jung | G01J 1/0411 | 250/226 |
| 6,304,324 B1* | 10/2001 | Iwasaki | G01J 3/02 | 356/213 |
| 9,001,333 B2* | 4/2015 | Endo | G01N 21/55 | 356/446 |
| 9,522,538 B2* | 12/2016 | Kuri | B41J 2/165 | |
| 9,797,774 B2* | 10/2017 | Sano | G01J 3/0272 | |
| 9,804,025 B2* | 10/2017 | Kanai | G01J 3/0208 | |
| 9,823,129 B2* | 11/2017 | Kuri | G01J 3/2823 | |
| 2004/0165177 A1* | 8/2004 | Katz | B24B 37/013 | 356/72 |
| 2004/0213433 A1* | 10/2004 | Noffke | B41F 33/0036 | 382/112 |
| 2004/0213436 A1* | 10/2004 | Noffke | B41F 33/0036 | 382/112 |
| 2006/0164657 A1* | 7/2006 | Chalmers | G01B 11/0625 | 356/630 |
| 2008/0309921 A1* | 12/2008 | Faase | G01J 3/02 | 356/73 |
| 2010/0296099 A1* | 11/2010 | Van Brocklin | B41J 29/393 | 356/456 |
| 2011/0063615 A1* | 3/2011 | Shimbo | G01J 3/02 | 356/326 |
| 2011/0090297 A1* | 4/2011 | Arai | G03G 15/04072 | 347/224 |
| 2011/0216315 A1* | 9/2011 | Uematsu | G01J 3/02 | 356/326 |
| 2011/0282613 A1* | 11/2011 | Skinner | G01J 3/50 | 702/104 |
| 2012/0008141 A1* | 1/2012 | Matsushita | G02B 5/284 | 356/326 |
| 2012/0133948 A1* | 5/2012 | Funamoto | G01J 3/0205 | 356/451 |
| 2013/0106959 A1* | 5/2013 | Kitada | B41J 2/1645 | 347/71 |
| 2013/0107260 A1* | 5/2013 | Nozawa | G01J 3/42 | 356/402 |
| 2013/0127946 A1* | 5/2013 | Kanai | B41J 2/125 | 347/19 |
| 2013/0286306 A1* | 10/2013 | Eiyama | B41J 29/393 | 349/19 |
| 2013/0314682 A1* | 11/2013 | Kemmoku | G03G 15/043 | 355/68 |
| 2014/0092479 A1* | 4/2014 | Nishimura | G02B 26/001 | 359/578 |
| 2014/0192357 A1* | 7/2014 | Sano | G01J 3/26 | 356/402 |
| 2014/0218734 A1* | 8/2014 | Shimaoka | G07D 7/121 | 356/369 |
| 2014/0240708 A1* | 8/2014 | Matsushita | G01J 3/26 | 356/402 |
| 2014/0240711 A1* | 8/2014 | Matsushita | G01J 3/0205 | 356/451 |
| 2014/0253924 A1* | 9/2014 | Sano | G01J 3/2823 | 356/456 |
| 2014/0267459 A1* | 9/2014 | Kanai | G01J 3/0218 | 345/690 |
| 2014/0285798 A1* | 9/2014 | Nishimura | G01J 3/26 | 356/300 |
| 2015/0369663 A1* | 12/2015 | Margalit | G01J 3/26 | 356/326 |
| 2016/0261774 A1* | 9/2016 | Kuri | G01J 3/463 | |
| 2016/0282182 A1* | 9/2016 | Kanai | G01J 3/26 | |
| 2016/0286054 A1* | 9/2016 | Kuri | H04N 1/00023 | |
| 2016/0363760 A1* | 12/2016 | Matsushita | G01J 3/26 | |
| 2016/0379095 A1* | 12/2016 | Nozawa | H04N 1/00023 | 358/1.9 |
| 2017/0122864 A1* | 5/2017 | Gomi | G01J 3/0289 | |
| 2017/0334220 A1* | 11/2017 | Tatsuda | B41J 13/0009 | |
| 2017/0334221 A1* | 11/2017 | Gomi | B41J 13/0009 | |

* cited by examiner

MEASURING DEVICE AND PRINTING APPARATUS

BACKGROUND

1. Technical Field

The invention relates to a measuring device, a printing apparatus, and the like.

2. Related Art

In the related art, an image forming device that forms an image on a recording medium (media), performs color measurement on the formed image, and corrects image formation conditions according to the color measurement result is known (for example, See JP-A-2013-117632).

The image forming device described in JPA-2013-117632 is a so-called electrophotographic image forming device in which an electrostatic latent image formed on a photosensitive drum is developed as a toner image, the toner image is transferred to the recording medium, and the toner image is fixed. The image forming device includes a front surface side irradiation unit which irradiates the image formation surface (front surface) side of a recording medium after the image fixation with light and a front surface side light receiving unit disposed in the surface side of the recording medium and measuring light from the recording medium. The image forming device further includes a pair of a black backing unit, and a white backing unit installed to be fixed as a background when performing color measurement, and a rear surface side irradiation unit which irradiates the non-image formation surface (rear surface) side of the recording medium with light. The pair of the black backing unit and the white backing unit, and the rear surface side irradiation unit are disposed on the rear surface side of the recording medium along a transport direction of the recording medium. The rear surface side irradiation unit and the front surface side light receiving unit are configured to be movable in the transport direction.

For example, in a case where printed matter in which an image is formed on a medium having translucency is observed in a state where transmitted light from a rear surface side of the medium is present, the light quantity from the printed matter may be increased by an influence of the transmitted light compared to a case where the printed matter in which an image is printed on a medium having low translucency under the same printing conditions is observed. In contrast, in the apparatus described in JP-A-2013-117632 described above, the surface side light receiving unit faces any of the black backing unit, the white backing unit, and the rear surface side irradiation unit according to the observation conditions and a type of a backing is set. With this, a relationship between an irradiation quantity of light from a surface and an irradiation quantity of light from a rear surface with respect to the recording medium is made equal to that of an actual observation so as to acquire a color measurement result in accordance with the observation conditions, and correct the image formation conditions based on the color measurement result.

However, in the apparatus described in JPA-2013-117632 described above, only the pair of the black backing unit, the white backing unit, and the rear surface side irradiation unit are present for the surface side light receiving unit and thus, measuring places are limited according to each of measurement conditions. When a plurality of color measurement patches are measured, a plurality of color measurement patches need to be printed along the transport direction of a medium, and media consumption is increased, resulting in an increase in running costs.

On the contrary, the color measurement patches also being provided in a direction (referred to as an intersecting direction) intersecting the transport direction of the medium to thereby improve the utilization efficiency of the medium may be considered. However, in the apparatus described in JP-A-2013-117632, the measuring place changes and thus, a moving mechanism which moves the front surface side irradiation unit, the front surface side light receiving unit, the black backing unit, the white backing unit, and the rear surface side irradiation unit in the intersecting direction needs to be provided and the number of components is increased. Therefore, there is a problem to be solved that the apparatus becomes complicated and larger and manufacturing costs are also increased.

SUMMARY

An advantage of some aspects of the invention is to provide a measuring device capable of measuring a plurality of color measurement patches with a simple configuration and a printing apparatus.

The measuring device according to an application example of the invention includes a spectrometer which is relatively movable between media having a first surface and a second surface which is a side opposite to the first surface and a holding unit holding the second surface of the media. The holding unit includes a plurality of light transmitting units transmitting light.

In the application example, the spectrometer is relatively movable between media and the holding unit includes a plurality of light transmitting units.

In a case where an image formed on a transparent media (in the following, referred to also as a transparent media) having high translucency is observed in a state where the transmitted light from the rear surface side of the media is incident on the second surface, a quantity of light from the media may be further increased and a light quantity (for example, the light quantity of received light of a light receiving element) of measured light may be increased compared to a case where an image formed on a non-transparent media (in the following, referred to also as an opaque media) is observed. In contrast, in the application example, for example, even in a case where spectrometry on a transparent media is conducted, the spectrometry is able to be conducted in a state where the rear surface side is irradiated with light which is transmitted through the light transmitting unit and thus, it is possible to inhibit a color change of an image and improve color reproducibility in accordance with translucency and the observation conditions of the media described above. For that reason, a color of an image can be measured with high accuracy.

In the application example, a plurality of color measurement patches can be measured with a simple configuration. That is, as a configuration in which the spectrometer is movable with respect to the media, for example, a configuration in which the measurement position of the spectrometer is movable to each measurement position (in the following, referred to also as a first measurement position) which overlaps a plurality of light transmitting units of a surface of the media and each measurement position (in the following, referred to also as a second measurement position) which does not overlap the plurality of light transmitting units may be included. In a case where the media is a transparent media, the spectrometer is moved to the first measurement position and spectrometry is conducted using a measurement pattern (in the following, referred to also as a first pattern) in which a plurality of color measurement patches are arranged to be overlapped with any of the first measurement positions. In a case where the media is an opaque media, the spectrometry is similarly conducted in second measurement positions using a measurement pattern (in the following, referred to also as a second pattern) in which a plurality of color measurement patches arranged to be overlapped with any of the second measurement positions.

In a configuration in which the media is movable with respect to the spectrometer, for example, a spectrometer capable of simultaneously measuring respective first measurement positions and respective second measurement positions may be used. Similar to the case described above, in a case of a transparent media, the first pattern is subjected to spectrometry in the respective first measurement positions and in a case of the opaque media, the second pattern is subjected to spectrometry in the respective second measurement positions.

As described above, in the application example, at least one of the spectrometer and the media is moved to thereby make it possible to conduct a measurement at a plurality of places, for example, even without installing a moving mechanism which moves the spectrometer and the holding unit simultaneously. According to the application example, the plurality of color measurement patches are able to be measured with a simple configuration. It is possible to prevent increase in running costs due to media consumption or increase in manufacturing costs due to increase in the number of components of an apparatus.

The measuring device of the application example preferably further includes a first light irradiation unit which irradiates the second surface side of the media with light from the light transmitting unit.

In the application example, the first light irradiation unit is provided to thereby make it possible to irradiate the second surface of the media with light of a predetermined light quantity from the light transmitting unit. The measurement accuracy in the measurement of the transparent media can be improved. In each of the plurality of light transmitting units, it is possible to make the light quantity of the transmitted light uniform. In particular, in a case where light is emitted from the rear surface side of the transparent media in which an image is formed using a backlight and the image is displayed, a color of the image is able to be measured with high accuracy.

The measuring device of the application example preferably further includes a second light irradiation unit which irradiates the first surface side of the media with light.

In the application example, the second light irradiation unit is provided to thereby make it possible to irradiate the first surface of the media with light having a predetermined light quantity. The measurement accuracy in the measurement of an opaque media can be improved.

In the application example of the measuring device, the holding unit is a plate-shaped member and the light transmitting unit is preferably a light-transmitting hole penetrating through the holding unit.

In the application example, the holding unit is the plate-shaped member and light having passed through the light-transmitting hole penetrating through the plate-shaped holding unit is incident on the second surface of the media. In the configuration described above, it is possible to hold the second surface of the media by a media side surface of the plate-shaped holding unit and easily maintain flatness of the first surface and the second surface of the media during measurement. It is possible to make light incident to the second surface while maintaining the flatness. It is possible to achieve improvement in the measurement accuracy of spectrometry.

In the measuring device of the application example, it is preferable that the holding unit includes a plurality of plate-shaped members and the light transmitting units includes a gap between one of the plurality of plate-shaped members and another one of the plurality of plate-shaped members.

In the application example, the holding unit includes a plurality of plate-shaped members and makes light having passed through the gap between the plate-shaped members incident to the second surface of the media. With this, it is possible to hold the second surface of the media by the media side surface of the plate-shaped holding unit and easily maintain flatness of the first surface and the second surface of the media during measurement. It is possible to make light incident to the second surface while maintaining the flatness. The improvement in the measurement accuracy of spectrometry can be achieved.

In the measuring device of the application example, the surface, which maintains at least the second surface of the media, of the holding unit is preferably white or black.

In the application example, the surface of the media side maintaining the second surface of the media of the holding unit is white or black. In this configuration, the measurement accuracy when an area other than the light transmitting unit of the holding unit is used as a backing is able to be improved. For example, when the light quantity from the media having translucency is measured, light transmitted through the media from the first surface side and reflected by the surface of the holding unit may be transmitted through the media again. Even in such a case, the surface of the holding unit is made white to thereby make it possible to prevent the light quantity of light reflected on the surface of the holding unit from being changed according to wavelength. The surface of the holding unit is made black to thereby make it possible to prevent light from being reflected on the surface of the holding unit and prevent degradation of the measurement accuracy caused by light reflected on the surface of the holding unit.

In the measuring device of the application example, a light quantity uniform optical system which makes a light quantity distribution of transmitted light uniform is preferably provided in the light transmitting unit.

In the application example, the light quantity uniform optical system is provided in the light transmitting unit. For that reason, it is possible to make light of which a distribution is uniform incident to the second surface of the media from the light transmitting unit and improve the color measurement accuracy when measuring the transparent media.

In the measuring device of the application example, it is preferable that a first light irradiation unit which irradiates the second surface side of the media with light is further provided and a type of media is determined based on the measurement result in the spectrometer when irradiation is performed with light from the first light irradiation unit.

In the application example, the type of media is determined based on the measurement result when irradiation is performed with light from the first light irradiation unit. For example, in a case of a transparent media having high translucency (for example, transmittance in the visible light region is 90% or more), light irradiated from the first light irradiation unit is transmitted to the first surface side. For that reason, the light quantity is increased by more than that in an opaque media having low translucency (for example, light transmittance in a visible light region is 10% or less). Accordingly, it is possible to easily determine a type of media based on the measurement result in the spectrometer, that is, a value of the light quantity.

The measuring device of the application example preferably includes a carriage on which the spectrometer is mounted and a moving mechanism which moves the carriage in one direction with respect to the media.

In the application example, the spectrometer is mounted on the carriage and a moving mechanism moving the carriage in one direction is provided. For that reason, it is possible to move the measurement position of the spectrometer in one direction with respect to the media. Accordingly, there may be a configuration in which the media is able to be transported in an intersecting direction intersecting with the one direction in order to change the measurement position of the spectrometer on the surface of the media two dimensionally, and an apparatus configuration may be simplified and the apparatus may be miniaturized by more than that in a configuration in which the media is able to be transported in both lights of the one direction and the intersecting direction.

In the measuring device of the application example, a plurality of light transmitting units are preferably disposed along the one direction.

In the application example, the spectrometer is configured to be movable in one direction and the plurality of light transmitting units are preferably disposed along the one direction which is a movement direction of the spectrometer.

In this configuration, for example, in a case of a transparent media, spectrometry of the color measurement patch formed in a position which overlaps the light transmitting unit along the one direction on the first surface of the transparent media is able to be conducted using the spectrometer. In a case of an opaque media, spectrometry of the color measurement patch formed in a position which does not overlap the light transmitting unit along the one direction on the first surface of the transparent media is able to be conducted using the spectrometer. With this, the spectrometry is able to be performed under the measurement conditions in accordance with translucency of the media or the observation conditions to acquire a color measurement result and color reproducibility of the image is able to be improved based on the color measurement result.

The spectrometry may be performed under the same measurement conditions in a plurality of positions along one direction which is the movement direction of the spectrometer. A plurality of color measurement patch columns, each of which includes a plurality of color measurement patches formed along one direction, are able to be formed in a direction (intersecting direction) intersecting the one direction, the spectrometry is able to be conducted in each of the plurality of positions by moving the spectrometer in one direction, and the media is able to be sent in the intersecting direction to change the color measurement patch column of a measurement target. With this, it is possible to prevent media consumption when the spectrometry is conducted on the plurality of color measurement patches and suppress increase in the running costs.

The printing apparatus according to the application example of the invention includes the measuring device of the application example and a printing unit forming an image on the media.

In the application example, spectrometry for the color measurement patch formed by the printing unit is able to be conducted by the measuring device. Accordingly, it is possible to change the printing conditions based on the measurement result and improve color reproducibility of an image.

The printing apparatus of the application example preferably includes a carriage on which the spectrometer and the printing unit are mounted.

In the application example, the spectrometer and the printing unit are mounted on a single carriage to thereby make it possible to simplify or miniaturize an apparatus configuration. The distance between the printing unit and the spectrometer is not changed and thus, it is possible to control respective positions of the printing unit and the spectrometer using the same coordinate system. With this, it is possible to reduce a processing load by more than that in a configuration in which positions of the printing unit and the spectrometer are controlled based on different coordinate systems, respectively, when the image printed by the printing unit is measured using the spectrometer.

In printing apparatus of the application example, in a case where the media is the transparent media, the printing unit preferably forms the color measurement patch in the area, which overlaps any of the plurality of light transmitting units, of the media and in a case where the media is the opaque media, the printing unit preferably forms the color measurement patch in the area, which does not overlap at least the light transmitting units, of the media.

In the application example, in a case of a transparent media, a color measurement patch is formed in the area which overlaps the light transmitting unit and in a case of the opaque media, the color measurement patch is formed in the area which does not overlap the light transmitting unit. In this configuration, it is possible to conduct spectrometry under the measurement conditions in accordance with the media type and the observation conditions.

The printing apparatus of the application example preferably further includes a parameter calculation unit calculating a color correction parameter when an image is formed by the printing unit, based on the result of the measurement of the spectrometer.

In the application example, the color correction parameter is calculated in the printing unit based on the measurement result of the spectrometer. In this configuration, it is possible to perform color correction using the color correction parameter in accordance with the observation conditions and improve color reproducibility of the image.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

Figure 1:
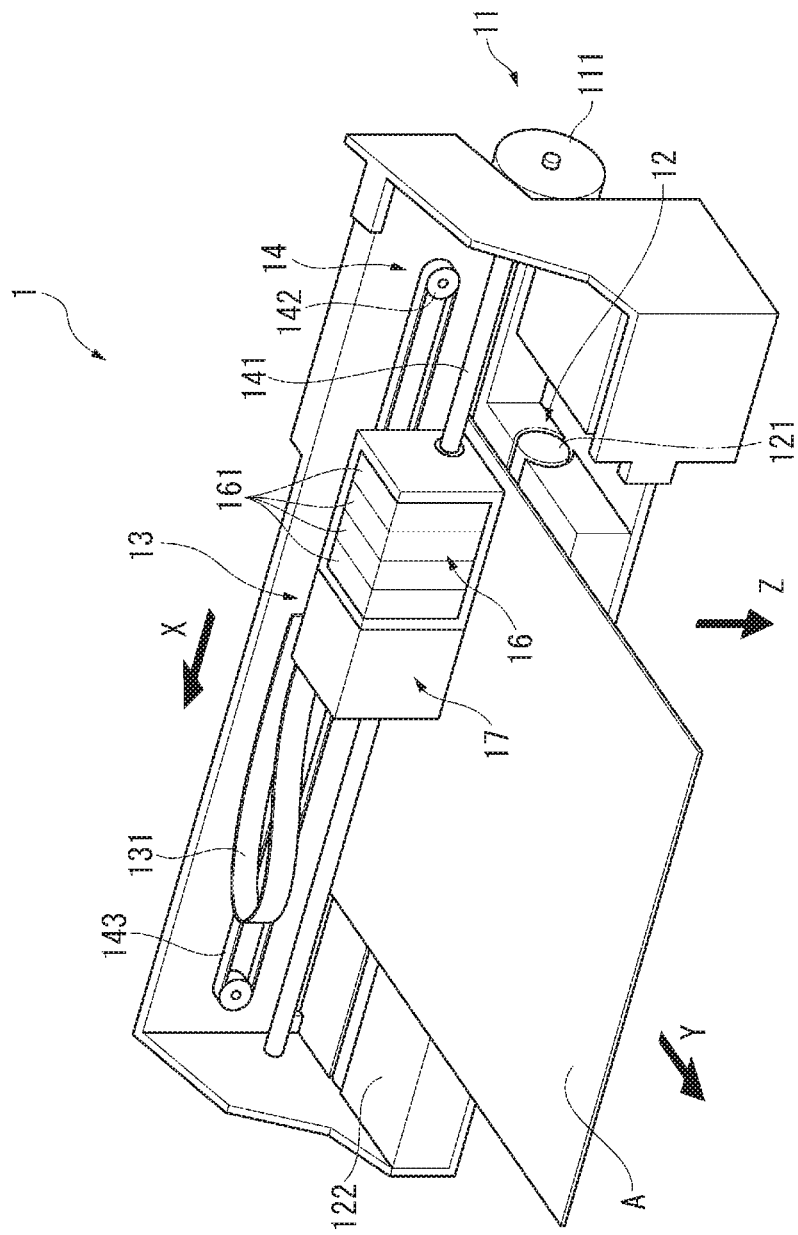
FIG. 1 is an appearance diagram illustrating a schematic configuration of a printer of a first embodiment according to the invention.
Figure 2:
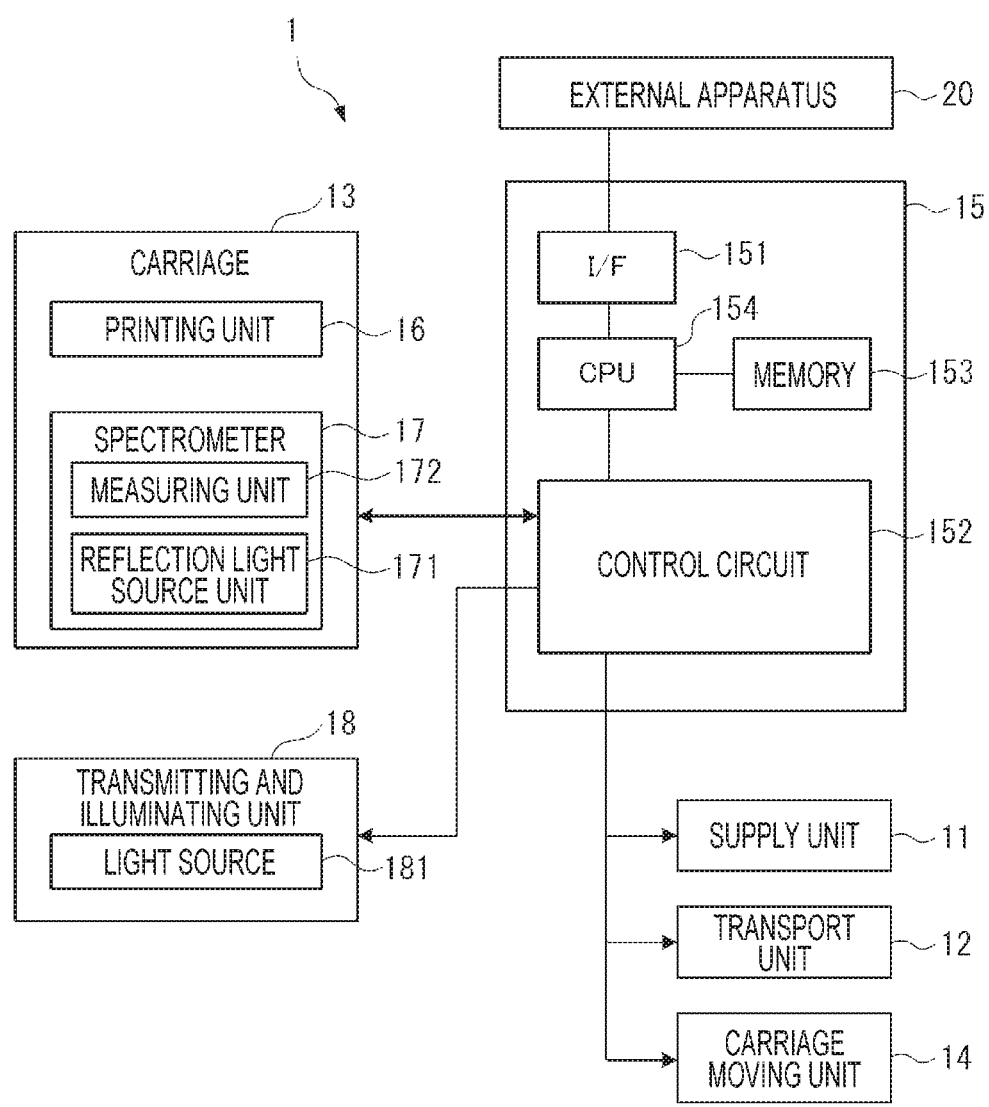
FIG. 2 is a block diagram illustrating the schematic configuration of the printer of a first embodiment.

In the following, a first embodiment according to the invention will be described based on the accompanying drawings. In the first embodiment, a printer 1 (inkjet printer) provided with a measuring device will be described in the following as an example of a printing apparatus according to an aspect of the invention.
Schematic Configuration of Printer FIG. 1 is an appearance diagram illustrating a schematic configuration of a printer 1 of the first embodiment. FIG. 2 is a block diagram illustrating the schematic configuration of the printer 1 of the first embodiment.

As illustrated in FIG. 1, the printer 1 includes a supply unit 11, a transport unit 12, a carriage 13, a carriage moving unit 14, a transmitting and illuminating unit 18, and a control unit 15 (see FIG. 2). The printer 1 controls respective units 11, 12, 14, and 18 and the carriage 13, and prints an image on a first surface (in the following, referred to as media surface A1) of media A, based on image data input from an external apparatus 20, for example, a personal computer. The printer 1 of the first embodiment prints a correction pattern including a plurality of color measurement patches disposed on predetermined positions on a media surface A1 based on print data for color correction and conducts spectrometry for the correction pattern. With this, the printer 1 generates a color correction parameter for correcting a color of image data for printing and performs the color correction on the image data for printing based on a measured value with respect to the color measurement patch. In the spectrometry, the printer 1 determines whether the media A has translucency or not. In a case where the media A does not have translucency, the printer 1 conducts measurement in a state where the media A is irradiated with illumination light from the media surface A1 side. In a case where the media A has translucency, the printer 1 conducts measurement in a state where the media A is irradiated with illumination light from a second surface (in the following, referred to as rear surface A2) of a side located opposite to the media surface A1. With this, a color correction parameter is acquired based on the measured value obtained by conducting spectrometry in accordance with translucency of the media A and the color correction of the image data for printing is conducted based on the color correction parameter.

In the following, respective configurations of the printer 1 will be specifically described.

The supply unit 11 is a unit to supply the media A (in the first embodiment, paper sheet is illustrated) which becomes an image formation target to an image formation position. The supply unit 11 includes, for example, a roll body 111 (see FIG. 1) around which the media A is wound, a roll driving motor (illustration is omitted), and roll driving wheel rows (illustration is omitted). The roll driving motor rotates based on the instruction from the control unit 15 and a rotational force of the roll driving motor is transferred to a roll body 111 through the roll driving wheel rows. With this, the roll body 111 rotates and the paper sheet wound around the roll body 111 is supplied downstream (+Y-direction) in the Y-direction (sub-scanning direction).

Although an example in which the paper sheet wound around the roll body 111 is supplied the roll body 111 is indicated, but the first embodiment is not limited thereto. For example, the media A may be supplied by any supplying method, for example, a method of supplying the media A such as paper sheets accumulated in a tray or the like, one by one by a roller or the like.

The transport unit 12 transports the media A supplied from the supply unit 11 along the Y-direction. The transport unit 12 is configured to include a transport roller 121, a driven roller (illustration is omitted) disposed to interpose the media A with the transport roller 121 and following the transport roller 121, and a platen 122.

A driving force is transferred to the transport roller 121 from the transport motor not illustrated and when the transport motor is driven by control of the control unit 15, the transport roller 121 rotates by the rotational force and transports the media A along the Y-direction while interposing the media A between the driven roller and the transport roller 121. The platen 122 opposing the carriage 13 is provided downstream (+Y side) of the transport roller 121 in the Y-direction. The platen 122 corresponds to the holding unit according to an aspect of the invention, abuts a surface of a side located opposite to the media surface A1 of the media A transported in the sub-scanning direction (Y-direction), and holds the media A.

Although a detailed configuration of the platen 122 will be describe later, a plurality of light transmitting units 123 each transmitting light from the transmitting and illuminating unit 18 toward the rear surface A2 of the media A are provided (see FIG. 5 and FIG. 6).

The carriage 13 includes a printing unit 16 that prints image on the media surface A1 of the media A and a spectrometer 17 that performs spectrometry for a predetermined measurement position of the media surface A1.

The carriage 13 is provided to be movable along the main scanning direction (X-direction) intersecting the Y-direction by the carriage moving unit 14.

The carriage 13 is connected to the control unit 15 by a flexible circuit 131 and conducts the print processing (image formation processing for the media surface A1) by the printing unit 16 and spectrometry by the spectrometer 17 based on the instruction from the control unit 15.

Detailed configuration of the carriage 13 will be described later.

The carriage moving unit 14 constitutes a moving mechanism according to an aspect of the invention and reciprocates the carriage 13 along the X-direction of based on the instruction from the control unit 15.

The carriage moving unit 14 is configured to include, for example, a carriage guide shaft 141, a carriage motor 142, and a timing belt 143.

The carriage guide shaft 141 is disposed along the X-direction and for example, both ends are fixed to a casing of the printer 1. The carriage motor 142 drives the timing belt 143. The timing belt 143 is supported in substantially parallel to the carriage guide shaft 141 and a portion of the carriage 13 is fixed thereto. When the carriage motor 142 is driven based on the instruction from the control unit 15, the timing belt 143 travels in the forward/reverse direction and the carriage 13 fixed to the timing belt 143 is guided by the carriage guide shaft 141 to be reciprocated.

Next, descriptions will be made on the configuration of the printing unit 16 and the spectrometer 17 provided on the carriage 13.

Configuration of Printing Unit

The printing unit 16 is provided to oppose the media A and ejects individually a plurality of color inks to the media surface A1 to form an image.

In the printing unit 16, ink cartridges 161 corresponding to a plurality of color inks are mounted removably and ink is supplied to a printer head (illustration is omitted) from each ink cartridge 161. On the bottom surface (a position opposing the media surface A1) of the printing unit 16, a nozzle (illustration is omitted) ejecting ink droplets is provided to correspond to each color. For example, a piezo-element is disposed on the nozzle and the piezo-element is driven so as to cause the ink droplets supplied from the ink tank to be landed on the media surface A1 and a toner image is formed.

Configuration of Spectrometer

Figure 3:
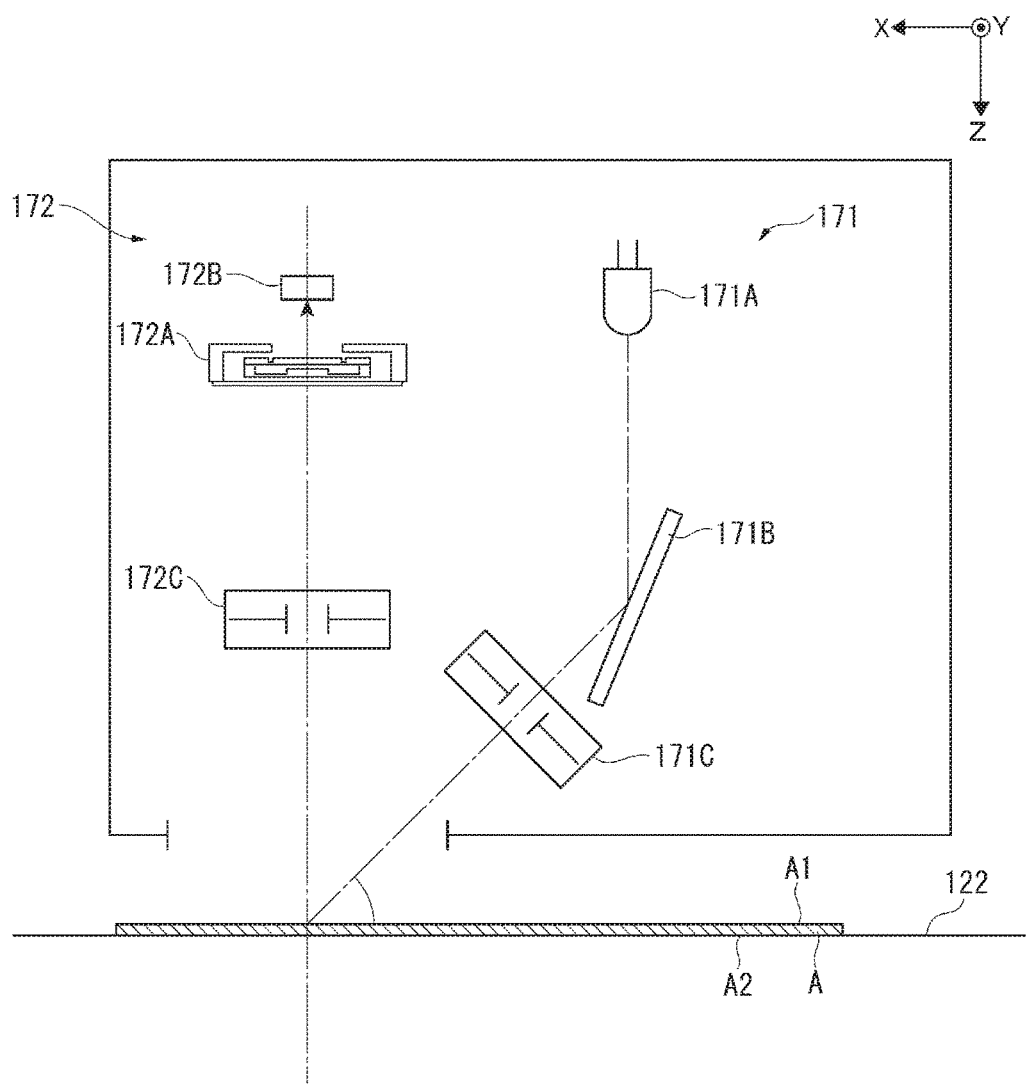
FIG. 3 is a sectional view illustrating a schematic configuration of a spectrometer of the first embodiment.

FIG. 3 is a sectional view illustrating a configuration of the spectrometer 17.

The spectrometer 17, as illustrated in FIG. 3, includes a reflection light source unit 171 and a measuring unit 172.

The spectrometer 17 irradiates the media A with illumination light from the reflection light source unit 171 and receives light reflected by a color measurement target (media surface A1, or calibration surface of calibration reference object or the like) by the measuring unit 172. A spectral device 172A provided in the measuring unit 172 is able to select the transmissive wavelength based on control of the control unit 15 and is able to measure a light quantity of light having respective wavelengths in the visible light region so as to make it possible to perform spectrometry of the measurement target. The spectrometry using the spectrometer 17 means spectrometry that measures the light quantity of respective spectral wavelengths contained in light reflected from the measurement target each.

In the first embodiment, spectrometry is conducted in compliance with a method in an optical-geometrical condition (45° x: 0°) specified by colorimetric standard (JISZ8722). That is, in the first embodiment, illumination light from the reflection light source unit 171 is made incident onto the measurement target at an incident angel of 45°±2° and receives light reflected in the normal direction at an angle of 0°±10° in the measurement target by the measuring unit 172.

In the first embodiment, for convenience of explanation, although a configuration in which the reflection light source unit 171 and the measuring unit 172 are parallel along the X-direction is illustrated, the configuration is not limited thereto. A configuration in which the reflection light source unit 171 and the measuring unit 172 are parallel along the Y-direction may be adopted or a configuration in which the reflection light source unit 171 and the measuring unit 172 are parallel along a direction intersecting the XY-direction may be adopted.

Configuration of Reflection Light Source Unit

As illustrated in FIG. 3, the reflection light source unit 171 corresponds to a second light irradiation unit according to an aspect of the invention and further includes a light source 171A, a reflection mirror 171B which reflects illumination light emitted from the light source 171A such that an incident angle to the media surface A1 of the media A becomes 45°, and an illumination light optical member 171C which guides the illumination light reflected by the reflection mirror 171B on the media surface A1. The reflection light source unit 171 irradiates a predetermined position on the media surface A1 with spot light (see front surface side illumination area Ar2 of FIG. 5).

The light source 171A is a member emitting illumination light, which falls in the visible light region, with which the media A is irradiated. In the first embodiment, a configuration in which the spectrometer 17 is mounted on the carriage 13 of the printer 1 is adopted, and the spectrometer 17 needs to be smaller in size and lighter in weight. For that reason, an LED or the like is preferably used as the light source 171A.

The illumination light optical member 171C emits illumination light toward the media A. In FIG. 3, an example in which the illumination light optical member 171C is provided between the reflection mirror 171B and the media A. However, the configuration is not limited thereto. For example, the illumination light optical member 171C may be provided between the light source 171A and the reflection mirror 171B. The illumination light optical member 171C may be configured by a single or a plurality of optical members. For example, a configuration in which a single or a plurality of apertures are provided as the illumination light optical member 171C and the media A is irradiated with illumination light having a predetermined light path diameter transmitted through the apertures may be illustrated. The apertures described above are provided so as to allow the predetermined position of the media A to be irradiated with the spot light. A collimator lens may be provided as the illumination light optical member 171C. In this case, the media A is able to be irradiated with parallel light beams from the reflection light source unit 171, and even in a case where the position of the media A is displaced in the Z direction, a size (spot diameter) of the front surface side illumination area Ar2 on the media A is allowed to become substantially constant.

The reflection light source unit 171 may have a configuration in which the reflection mirror 171B is not provided. For example, a configuration in which the light source 171A is disposed to allow the media surface A1 to be irradiated with illumination light at 45° and the configuration as described above is adopted so as to make it possible to reduce the number of components. In this case, apertures may be provided between the light source 171A and the media surface A1.

Configuration of Measuring Unit

The measuring unit 172, as illustrated in FIG. 3, is configured to include a spectral device 172A, a light receiving unit 172B, and a light reception optical member 172C.

In the measuring unit 172 described above, light reflected in the −Z direction in the media A is made incident on the spectral device 172A by the light reception optical member 172C and light of a predetermined wavelength dispersed by the spectral device 172A is received in the light receiving unit 172B.

The light reception optical member 172C is configured by a singular or a plurality of optical members. For example, a singular or a plurality of apertures may be illustrated as the light reception optical member 172C. The apertures described above are provided so as to make it possible to guide measurement light reflected in a predetermined measurement area Ar3 (see FIG. 5) on the media A to the spectral device 172A and the light receiving unit 172B. Although details will be described, in the first embodiment, the measurement area Ar3 has a size larger than that of the front surface side illumination area Ar2 and the front surface side illumination area Ar2 is included in the measurement area Ar3.

Furthermore, as the light reception optical member 172C, for example, a lens, which focuses measurement light from the measurement area Ar3 on the light receiving unit 172B, or the like may be provided. When the lens described above is used, even in a case where the aperture or the like is not provided, light from a predetermined measurement area Ar3 is able to be focused on the light receiving unit 172B. That is, it is possible to form the measurement area Ar3 having a desired size by the light reception optical member 172C. Furthermore, a configuration in which a bandpass filter is provided as the light reception optical member 172C and light other than the visible light is cut by the bandpass filter may be adopted.

Configuration of Spectral Device

Figure 4:
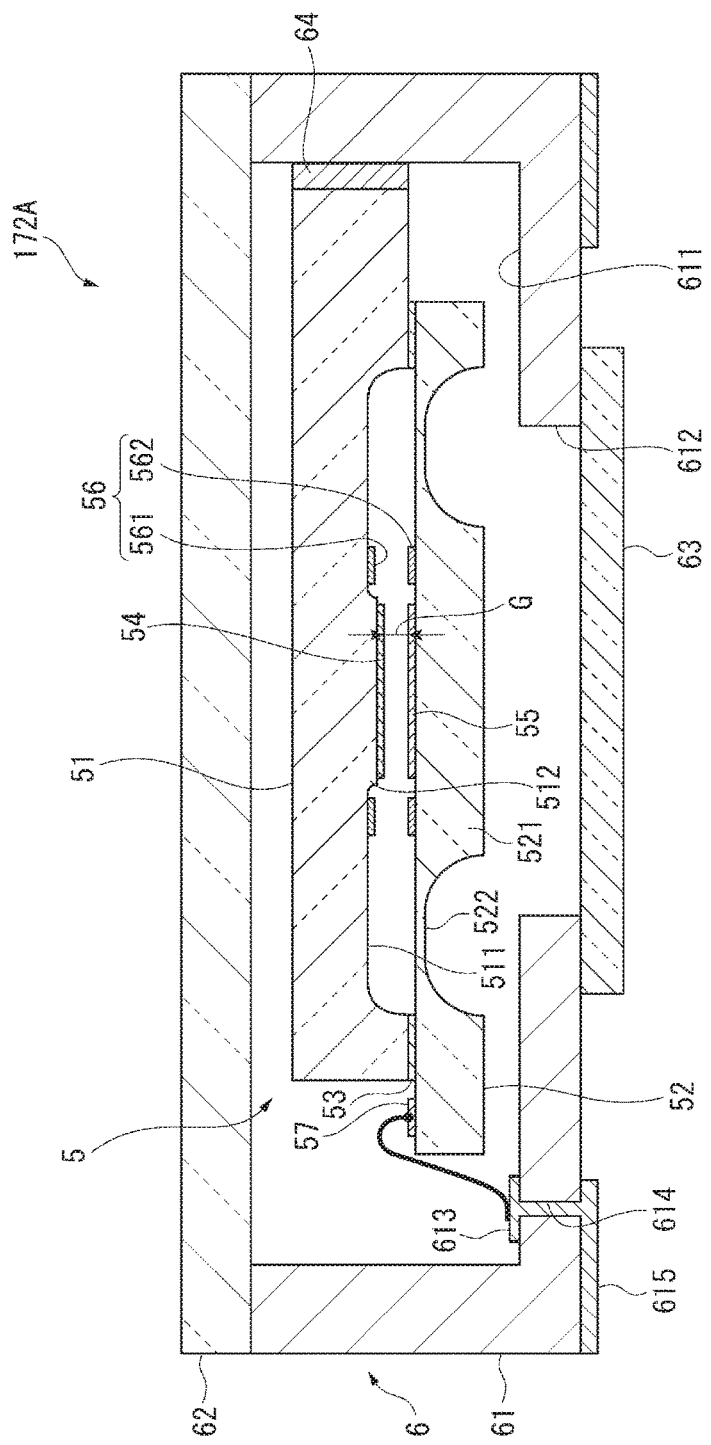
FIG. 4 is a sectional view illustrating a schematic configuration of an optical filter device of the first embodiment.

FIG. 4 is a sectional view illustrating a schematic configuration of the spectral device 172A.

The spectral device 172A includes a casing 6 and a wavelength variable interference filter 5 (spectral element) accommodated within the casing 6.

Configuration of Wavelength Variable Interference Filter

The wavelength variable interference filter 5 is a wavelength variable type Fabry-Perot etalon element and constitutes a spectral element according to an aspect of the invention. In the first embodiment, although an example in which the spectrometer 17 is disposed in a state where the wavelength variable interference filter 5 is accommodated in the casing 6, for example, a configuration in which the wavelength variable interference filter 5 is directly disposed in the spectrometer 17 may be adopted.

The wavelength variable interference filter 5, as illustrated in FIG. 4, includes the fixed substrate 51 having translucency and the movable substrate 52, and the fixed substrate 51 and the movable substrate 52 are bonded by a bonding film 53 to be integrally formed. In the fixed substrate 51, a first groove portion 511 formed by etching and a second groove portion 512 of which a depth of groove is shallower than the first groove portion 511 are provided. The fixed electrode 561 and the fixed reflection film 54 are provided on the first groove portion 511 and the second groove portion 512, respectively. For example, the fixed reflection film 54 is made up of a metal film such as Ag, an alloy film such as Ag alloy, a dielectric multiplayer film obtained by laminating a high-refraction layer and a low-refraction layer, or a laminate obtained by laminating a metal film (alloy film) and a dielectric multilayer film.

The movable substrate 52 includes a movable portion 521 and a holding unit 522 provided outside the movable portion 521 and holding the movable portion 521. On a surface opposing the fixed substrate 51 of the movable portion 521, a movable electrode 562 opposing a fixed electrode 561 and a movable reflection film 55 opposing the fixed reflection film 54 are provided. As the movable reflection film 55, a reflection film having the same configuration as the fixed reflection film 54 described above may be used. The holding unit 522 is a diaphragm surrounds a periphery of the movable portion 521 and is formed to have thickness dimension smaller than that of the movable portion 521.

In the wavelength variable interference filter 5 described above, an electrostatic actuator 56 is configured by the fixed electrode 561 and the movable electrode 562 and a voltage is applied to the electrostatic actuator 56 so as to make it possible to change gap dimension of a gap G between the fixed reflection film 54 and the movable reflection film 55. In the outer periphery (area which does not opposing fixed substrate 51) of the movable substrate 52, a plurality of electrode pads 57 individually connected to the fixed electrode 561 or the movable electrode 562 are provided.

Configuration of Casing

The casing 6, as illustrated in FIG. 4, includes a base 61 and a glass substrate 62. The base 61 and the glass substrate 62, for example, are bonded by low melting point glass bonding or the like to form an accommodation space inside thereof, and the wavelength variable interference filter 5 is accommodated within the accommodation space.

The base 61, for example, is configured by laminating thin plate-shaped ceramics and includes a concave portion 611 capable of accommodating the wavelength variable interference filter 5. The wavelength variable interference filter 5, for example, is fixed to a side surface of the concave portion 611 of the base 61 by a fixing member 64. On the bottom of the concave portion 611 of the base 61, a light-transmitting hole 612 is provided and a cover glass 63 covering the light-transmitting hole 612 is bonded.

In the base 61, an internal terminal portion 613 connected to the electrode pad 57 of the wavelength variable interference filter 5 is provided, and the internal terminal portion 613 is connected to an external terminal portion 615 provided outside of the base 61 through a conductive hole 614. The external terminal portion 615 is electrically connected to the control unit 15.

Configuration of Light Receiving Unit

Referring back to FIG. 3, the light receiving unit 172B is disposed on an optical axis (on a straight line passing the center points of reflection films 54 and 55) of the wavelength variable interference filter 5, light transmitted through the wavelength variable interference filter 5 is received in a light receiving area, and a detection signal (a current value) according to the quantity of received light is output. The detection signal output by the light receiving unit 172B is input to the control unit through an I-V converter (illustration is omitted), an amplifier (illustration is omitted), and an AD converter (illustration is omitted).

Configuration of Transmitting and Illuminating Unit

Figure 5:
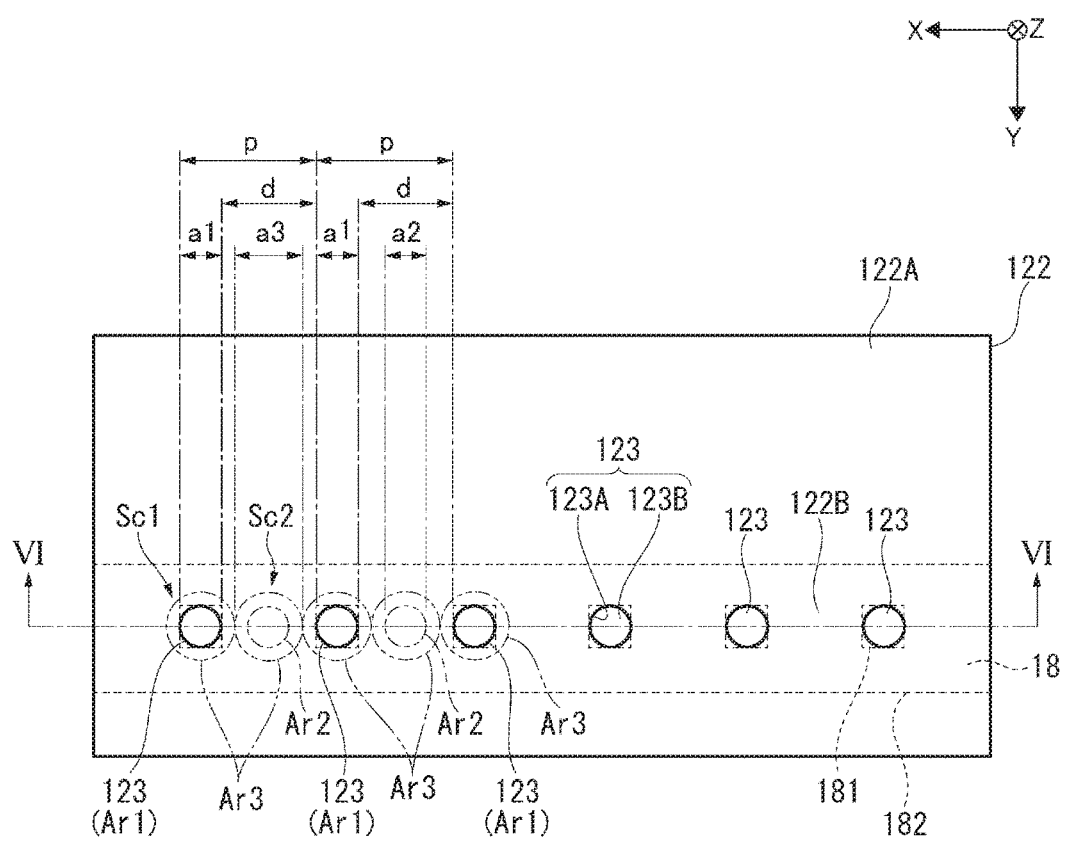
FIG. 5 is a plan view illustrating a schematic configuration of a platen of the first embodiment.
Figure 6:
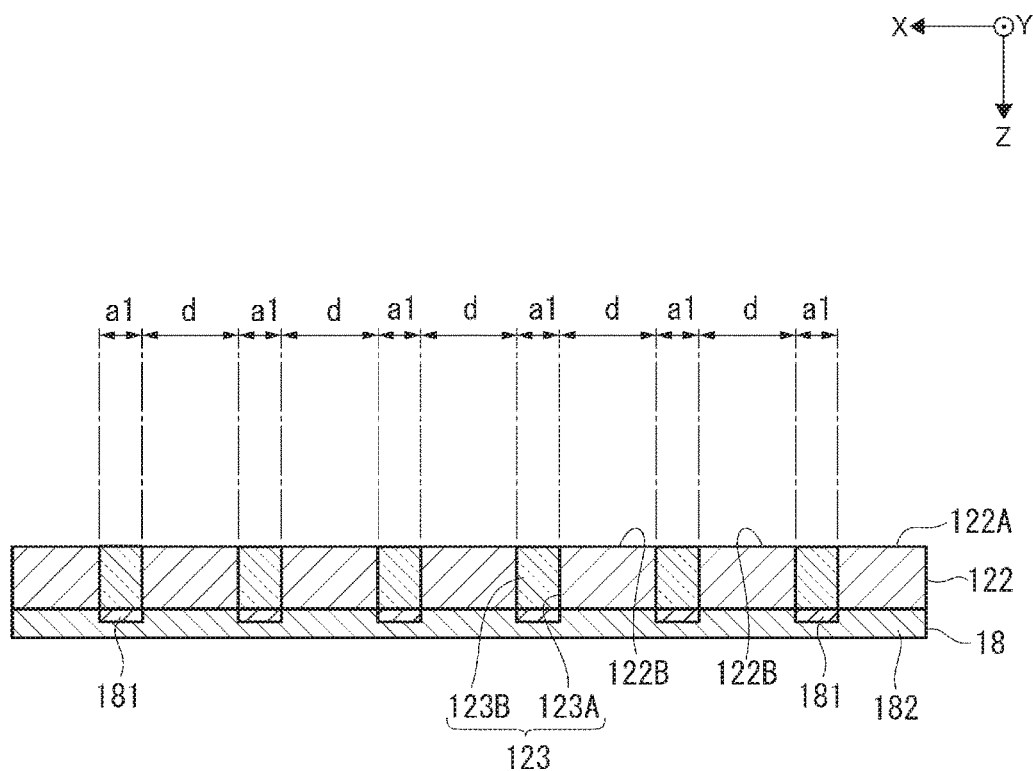
FIG. 6 is a sectional view illustrating a schematic configuration of the platen and a transmitting and illuminating unit of the first embodiment.

FIG. 5 is a plan view illustrating a schematic configuration of the platen 122 and the transmitting and illuminating unit 18 when viewed from the Z-direction. FIG. 6 is a sectional view illustrating the schematic configuration of the platen 122 and the transmitting and illuminating unit 18 when cut along the line VI-VI of FIG. 5. In FIG. 5, illustration of the transport roller 121 provided on the −Y side end portion of the platen 122 −Y side is omitted.

The transmitting and illuminating unit 18 corresponds to a first light irradiation unit according to an aspect of the invention and is disposed on the +Z side of the platen 122 and emits light toward the −Z direction based on control of the control unit 15. Light emitted from the transmitting and illuminating unit 18 passes through the light transmitting unit 123 of the platen 122 which will be described later and the rear surface A2 side and the rear surface A2 side of the media A is irradiated with the light. The transmitting and illuminating unit 18 includes a plurality of light sources 181 and an illumination unit substrate 182 provided with the light source 181.

The plurality of light source 181s are disposed on the +Z side of the illumination unit substrate 182 along the X-direction at regular intervals. The light source 181 is disposed at a position which overlaps the light transmitting unit 123 of the platen 122. A light source capable of emitting white light such as a halogen lamp or an LED may be used as the light source 181. In the first embodiment, the light source 181 is turned on in a case where spectrometry of the transparent media having high translucency which will be described later is conducted or the like. For that reason, the LED may be used as the light source 181 to thereby suppress variation in the light quantity immediately after turning-on of the LED.

The illumination unit substrate 182 is a circuit substrate provided with the light source 181 and may be appropriately provided in a light source driver circuit or the like.

Configuration of Platen

The platen 122 includes a holding surface 122A which abuts the rear surface A2 of the media A and holds the media A, and is provided with a plurality of light transmitting units 123 each transmits light emitted from the transmitting and illuminating unit 18 to the rear surface A2 side in the −Z direction and illuminates a predetermined area of the rear surface A2 (in the following, referred to also as rear front surface side illumination area Ar1).

A surface (backing surface) 122B, in which the light transmitting unit 123 is not provided, of the holding surface 122A, for example, is made white having reflectance of 80% or more with respect to each wavelength. With this, in a case where the measurement area Ar3 is set on the backing surface 122B to conduct spectrometry, reduction in the measurement accuracy may be suppressed. That is, even in a case where light which is transmitted through the media A, is reflected by the holding surface 122A, and is incident onto the measuring unit 172 exists, reduction in the measurement accuracy due to a difference in the light quantities of reflected light according to wavelengths may be suppressed. In the first embodiment, the backing surface 122B is made white, however, may also be made black (for example, having reflectance of 5% or less of each wavelength). In this case, generation of reflected light may be suppressed and thus, similarly, reduction in the measurement accuracy may be suppressed. The backing surface 122B may be made a color having a known reflectance other than white or black.

Each light transmitting unit 123 is configured by a light-transmitting hole 123A penetrating through the platen 122 along the Z direction and a light quantity uniform optical member 123B disposed in the light-transmitting hole 123A.

The light quantity uniform optical member 123B corresponds to a light quantity uniform optical system according to an aspect of the invention and is an optical member which irradiates the rear surface A2 with light emitted from the light source 181 of the transmitting and illuminating unit 18 as light having uniform light quantity distribution in the XY plane. The light quantity uniform optical member 123B is able to be configured by a single or a plurality of optical members and a diffusion plate is used in the first embodiment. The diffusion plate has a function of diffusing light which has entered. For example, a diffusion plate having a configuration in which particles, of which the refraction ratio is different from that of base material such as quarts glass or acrylic, are dispersed may be used. The diffusion plate described above is used to thereby make it possible to irradiate the rear surface A2 with light having uniform light quantity distribution by a simple configuration.

A collimator may be provided as the light quantity uniform optical member 123B on the +Z side of the diffusion plate. In this case, it is possible to prevent diffusion of light emitted from the light transmitting unit 123 and set a desired value as a size (spot diameter) of the rear front surface side illumination area Ar1 on the rear surface A2. As the light quantity uniform optical member 123B, various optical systems capable of substantially making in-plane light quantity distribution of the integrator optical system or the like uniform may also be used.

The light transmitting unit 123, as illustrated in FIG. 5, is provided in such a way that a center position of a measurement area Ar3 coincides with a center position of the light transmitting unit 123 (rear front surface side illumination area Ar1) in the Y-direction in plan view when viewed from the Z direction. The plurality of light transmitting units 123 are provided along the X-direction at regular intervals. In the first embodiment, the media A is tightly attached to the holding surface 122A of the platen 122 and thus, outer diameters of the light transmitting unit 123 and the rear front surface side illumination area Ar1 are substantially the same.

Here, spot diameters of the rear front surface side illumination area Ar1, the front surface side illumination area Ar2, and the measurement area Ar3 are respectively set as a1, a2, and a3, and a gap between the rear front surface side illumination areas Ar1 (light transmitting units 123) is set as d, and an arranging pitch of the rear front surface side illumination area Ar1 (light transmitting unit 123) is set as p. In the first embodiment, these respective values are set to satisfy the following expressions (1) to (4).

$$d > a3 \quad (1)$$

$$a3 > a1 \quad (2)$$

$$a1 \approx a2 \quad (3)$$

$$p \approx a3 \times 2 \quad (4)$$

As represented in the expression (1), the gap d between the rear front surface side illumination areas Ar1 (light transmitting unit 123) is greater than the diameter a3 of the measurement area Ar3. Accordingly, the carriage is moved along the X-direction to thereby make it possible to select two positions on a position (in the following, referred to also as first measurement position) Sc1 at which the measurement area Ar3 overlaps the rear front surface side illumination area Ar1 and a position (in the following, referred to also as second measurement position) Sc2 at which the measurement area Ar3 does not overlap the rear front surface side illumination area Ar1 (see FIG. 5). That is, spectrometry is able to be conducted under two different measurement conditions. At the first measurement position, spectrometry is able to be conducted under the condition in which the transmitting and illuminating unit 18 is driven and illumination light from the rear surface A2 side is emitted and at the second measurement position, spectrometry is able to be conducted under the condition in which illumination light from the rear surface A2 side is not emitted.

As will be described later, in the first embodiment, in a case where the media A is transparent media having translucency higher than a predetermined value, a color correction parameter is calculated using a result of the spectrometry of a first correction pattern 31 (see FIG. 11) in which the color measurement patches 30 are arranged to include the first measurement position Sc1 (rear front surface side illumination area Ar1). On the other hand, in a case where the media A is opaque media having translucency lower than the predetermined value, the color correction parameter is calculated using a result of the spectrometry of a second correction pattern 32 (see FIG. 12) in which the color measurement patches 30 are arranged to include the second measurement position Sc2.

As represented in the expression (2), the diameter a3 of the measurement area Ar3 is greater than the spot diameter a1 of the rear front surface side illumination area Ar1 and thus, spectrometry is conducted using light passing through a central portion of the measurement area Ar3, that is, central portions having relatively high parallelism of respective reflection films 54 and 55 of the wavelength variable interference filter 5. With this, the measurement accuracy is able to be improved.

In the first embodiment, as represented in the expression (3), the spot diameters a1 and a2 of the rear front surface side illumination area Ar1 and the front surface side illumination area Ar2 are set to be equal, and as represented in the expression (4), the arranging pitch p is set to be twice the diameter a3 of the measurement area Ar3. With this, as illustrated in FIG. 5, it is possible to set the plurality of measurement areas Ar3 to be adjacent to each other in the X-direction and increase the number of the measurement positions in the X-direction.

Configuration of Control Unit

As illustrated in FIG. 2, the control unit 15 is configured to include an I/F 151, a control circuit 152, a memory 153, and a central processing unit (CPU) 154.

The I/F 151 inputs image data input from the external apparatus 20 to the CPU 154.

The control circuit 152 includes control circuits which respectively control the supply unit 11, the transport unit 12, the printing unit 16, the light source 171A, the wavelength variable interference filter 5, the light receiving unit 172B, the carriage moving unit 14, and the transmitting and illuminating unit 18, and controls operations of respective units based on instruction signals of the CPU 154. The control circuit of respective units may be provided in an object separate from the control unit 15 and connected to the control unit 15.

The memory 153 stores various programs used for controlling operations of the printer 1 or various types of data.

Various types of data may include, for example, V-λ data indicating a wavelength of light transmitted through the wavelength variable interference filter 5 with respect to an applied voltage to the electrostatic actuator 56 when the wavelength variable interference filter 5 is controlled, various parameters converting colors contained in the image data into an ejection amount of each ink, or the like. The memory 153 may store light emission characteristics with respect to each wavelength of the light source 171A or light-receiving characteristics (light-receiving sensitivity characteristics) with respect to each wavelength of the light receiving unit 172B.

Figure 7:
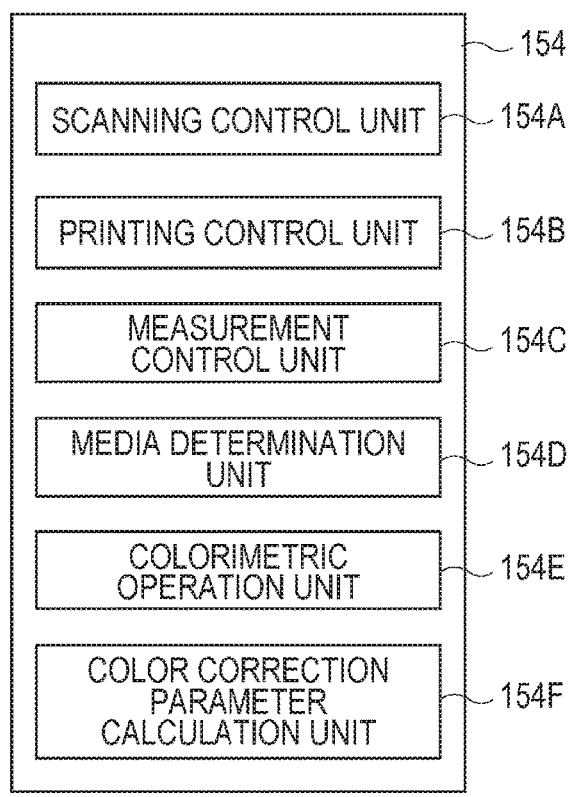
FIG. 7 is a block diagram illustrating a functional configuration of a CPU included in a control unit of the first embodiment.

FIG. 7 is a block diagram illustrating a functional configuration of the CPU 154 included in the control unit 15 of the printer 1.

The CPU 154 reads and executes various programs stored in the memory 153 to function as a scanning control unit 154A, a printing control unit 154B, a measurement control unit 154C, a media determination unit 154D, a color measurement operation unit 154E, and a color correction parameter calculation unit 154F or the like as illustrated in FIG. 7.

The scanning control unit 154A outputs instruction signals to drive the supply unit 11, the transport unit 12, and the carriage moving unit 14 to the control circuit 152. With this, the control circuit 152 drives the roll driving motor of the supply unit 11 to supply the media A to the transport unit 12. The control circuit 152 drives the transport motor of the transport unit 12 to transport a predetermined area of the media A along the Y-direction until the predetermined area reaches a position opposing the carriage 13 of the platen 122. The control circuit 152 drives the carriage motor 142 of the carriage moving unit 14 to move the carriage 13 along the X-direction.

The printing control unit 154B, for example, outputs the instruction signal to control the printing unit 16 to the control circuit 152 based on the image data input from the external apparatus 20. When the instruction signal is output from the printing control unit 154B to the control circuit 152, the control circuit 152 outputs a print control signal to the printing unit 16 and drives the piezo-element provided in the nozzle to cause inks to be ejected to the media A. When printing is conducted, the carriage 13 is moved along the X-direction, a dot formation operation in which inks are ejected from the printing unit 16 during the movement and a transport operation for transporting the media A in the Y-direction are alternately repeated, and an image formed by a plurality of dots are printed on the media A.

The printing control unit 154B conducts various processing on the image data and generates print data representing a recording density of ink droplets as the instruction signal. Here, the image data, for example, corresponds to RGB data represented by color coordinates of R (red), G (green), and B (blue). In a case where printing is performed using respective color inks of C (cyan), M (magenta), Y (yellow), and K (black), the printing control unit 154B converts the image data from the RGB data to CMYK data represented by the CMYK color coordinate system (color coordinate conversion). The printing control unit 154B performs half-tone processing on the CMYK data to convert the CMYK data into print data, and controls the printing unit 16 based on the print data to print an image.

The measurement control unit 154C conducts spectrometry. Specifically, in a case where the type of the media A is the opaque media, the measurement control unit 154C outputs the instruction signal to control the light source 171A to the control circuit 152 and causes the light source 171A to emit light. In a case where the type of the media A is the transparent media, the measurement control unit 154C outputs the instruction signal to control the light source 181 to the control circuit 152 and causes the light source 181 to emit light.

The measurement control unit 154C reads a driving voltage to the electrostatic actuator 56 with respect to the wavelength of light transmitted through the wavelength variable interference filter 5 from the V-λ data of the memory 153, and outputs the instruction signal to the control circuit 152. With this, the control circuit 152 applies the driving voltage, which is instructed from the measurement control unit 154C, to the wavelength variable interference filter 5 and light having a desired transmission parameter is transmitted from the wavelength variable interference filter 5.

The measurement control unit 154C associates a measured value in accordance with the light quantity (quantity of received light) of light received by the light receiving unit 172B with a voltage applied to the electrostatic actuator 56 (otherwise, wavelength of light transmitted through the wavelength variable interference filter 5 corresponding to the voltage) to be stored in the memory 153.

In a case where illumination is made from the rear surface A2 by the transmitting and illuminating unit 18 and in a case where illumination is not made, the media determination unit 154D determines whether the type of the media A is the transparent media or the opaque media based on the light quantity acquired by the measurement control unit 154C.

The color measurement operation unit 154E measures chromaticity with respect to the measurement area Ar3 based on the quantity of received light with respect to light of a plurality of wavelengths obtained by spectrometry.

The color correction parameter calculation unit 154F calculates the color correction parameter based on the color measurement result of the correction pattern by the color measurement operation unit 154E.

Print Processing

Next, description will be made on the print processing of the image by the printer 1 of the first embodiment based on the drawings.

Figure 8:
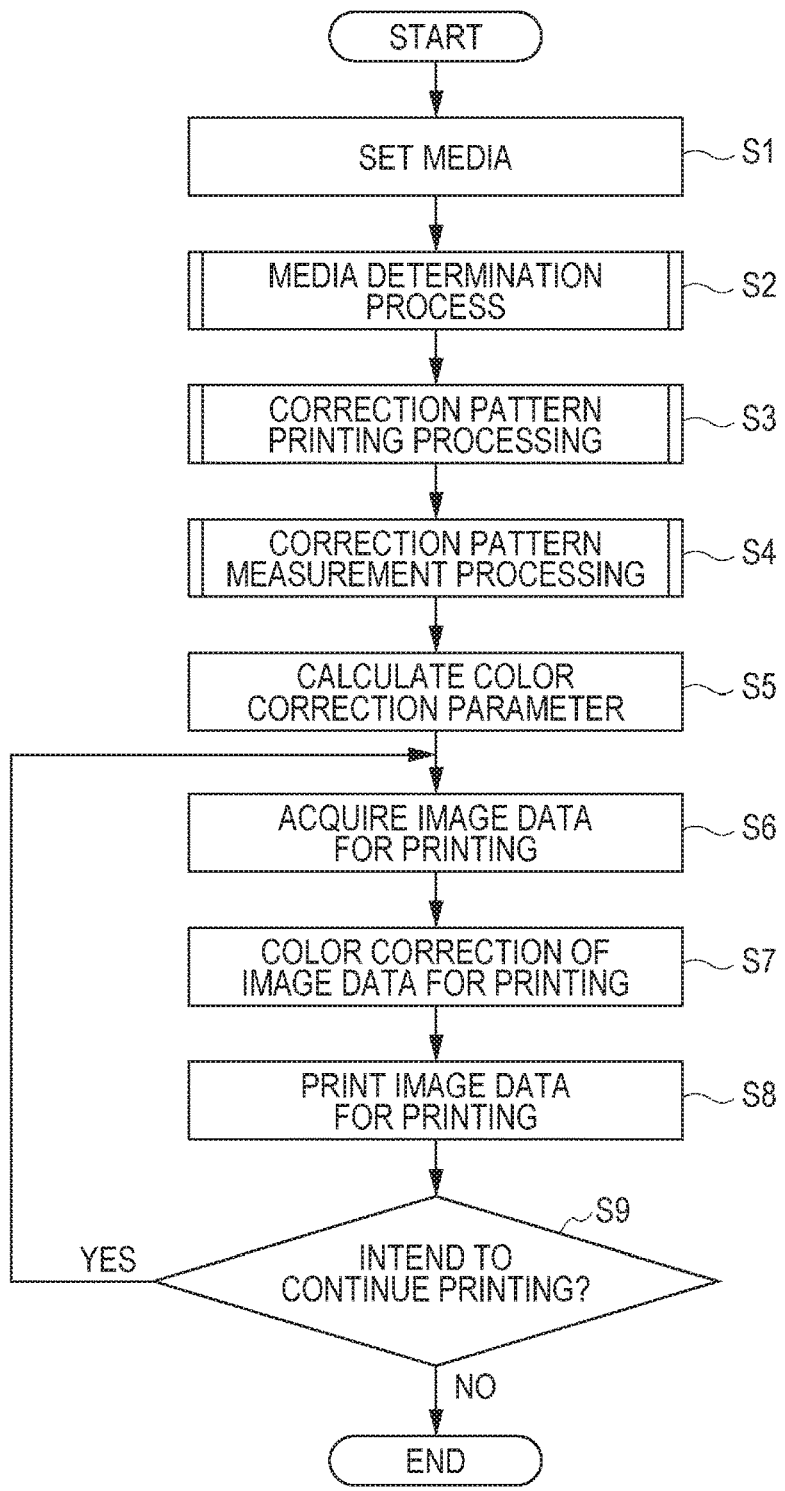
FIG. 8 is a flowchart illustrating an example of print processing in the first embodiment.
Figure 9:
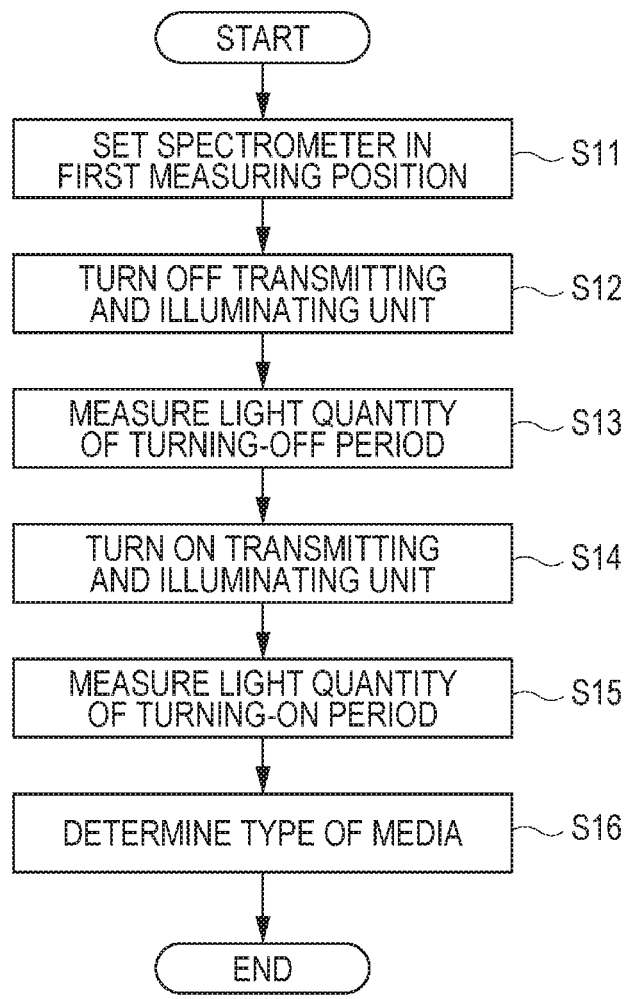
FIG. 9 is a flowchart illustrating an example of media determination processing of the first embodiment.
Figure 10:
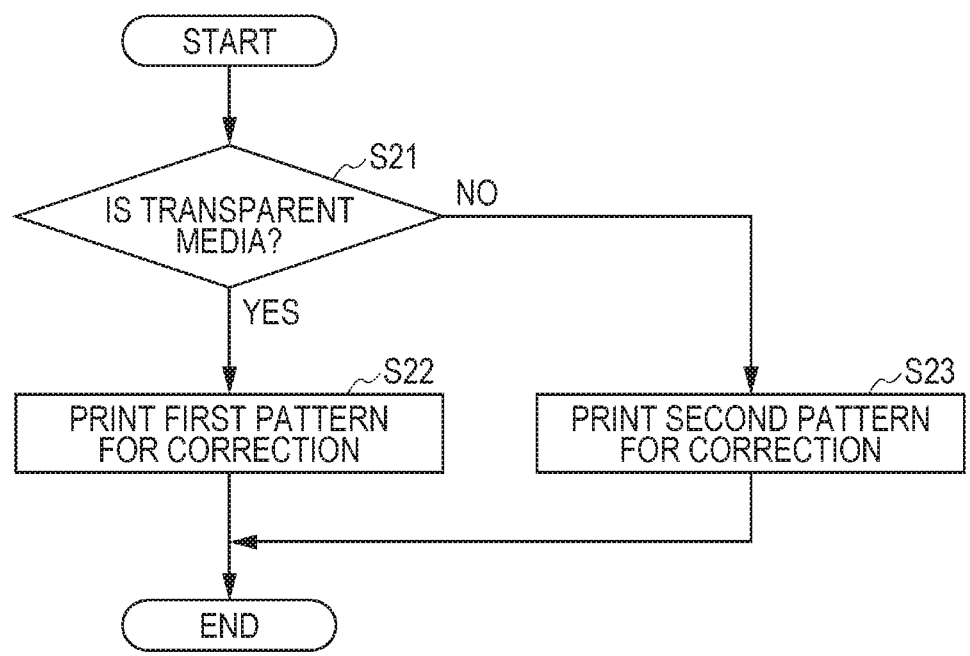
FIG. 10 is a flowchart illustrating an example of correction pattern printing processing of the first embodiment.
Figure 11:
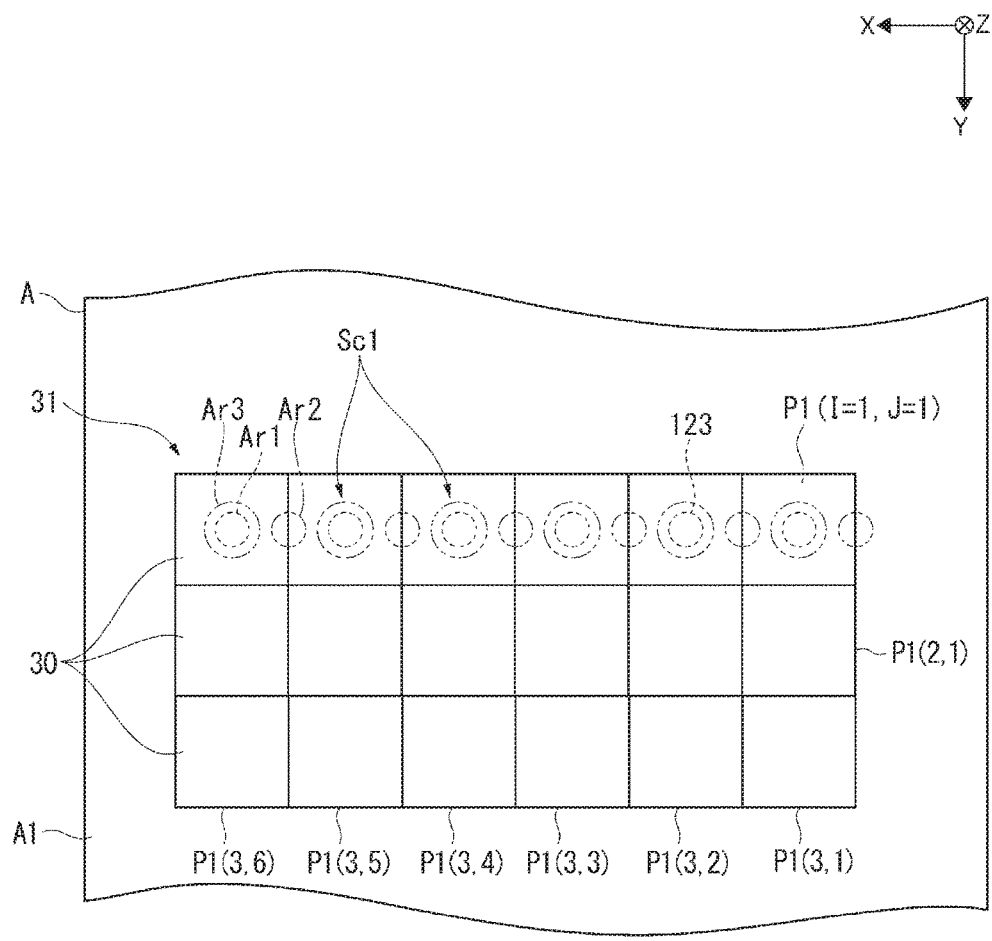
FIG. 11 is a diagram schematically illustrating an example of a first correction pattern in the first embodiment.
Figure 12:
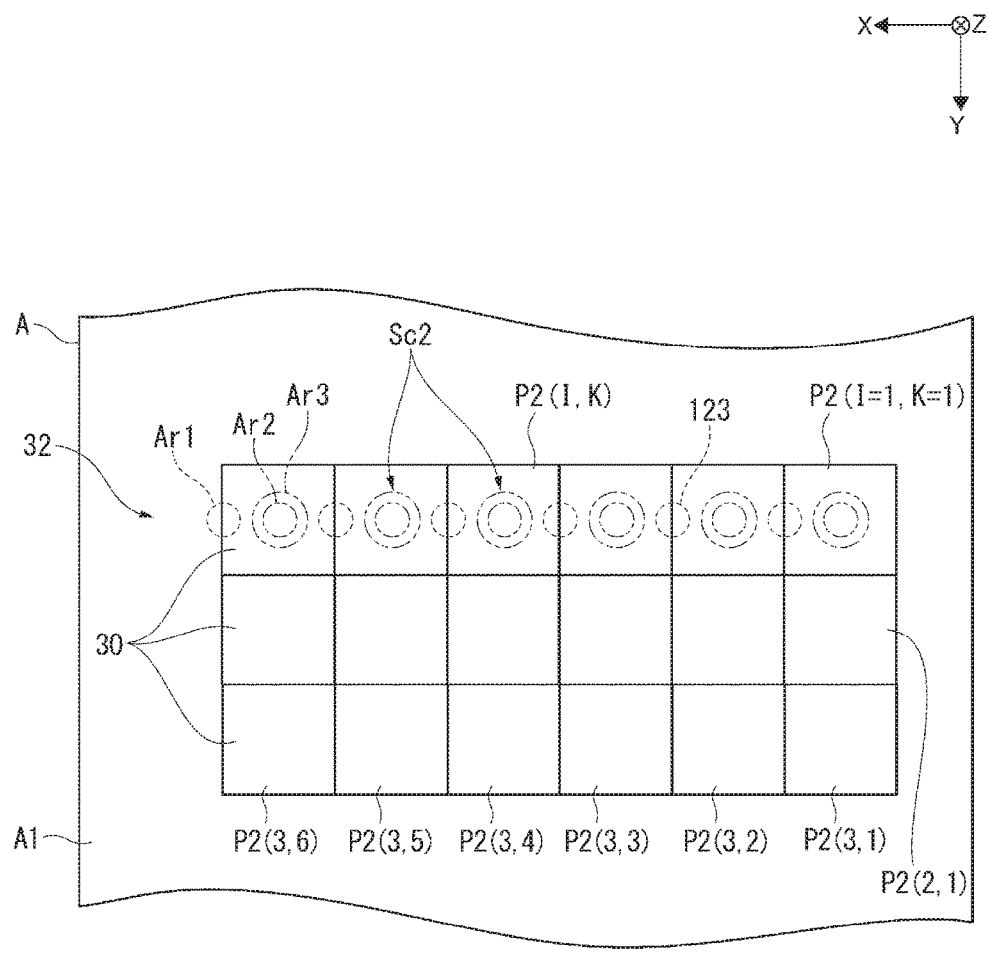
FIG. 12 is a diagram schematically illustrating an example of a second correction pattern in the first embodiment.
Figure 13:
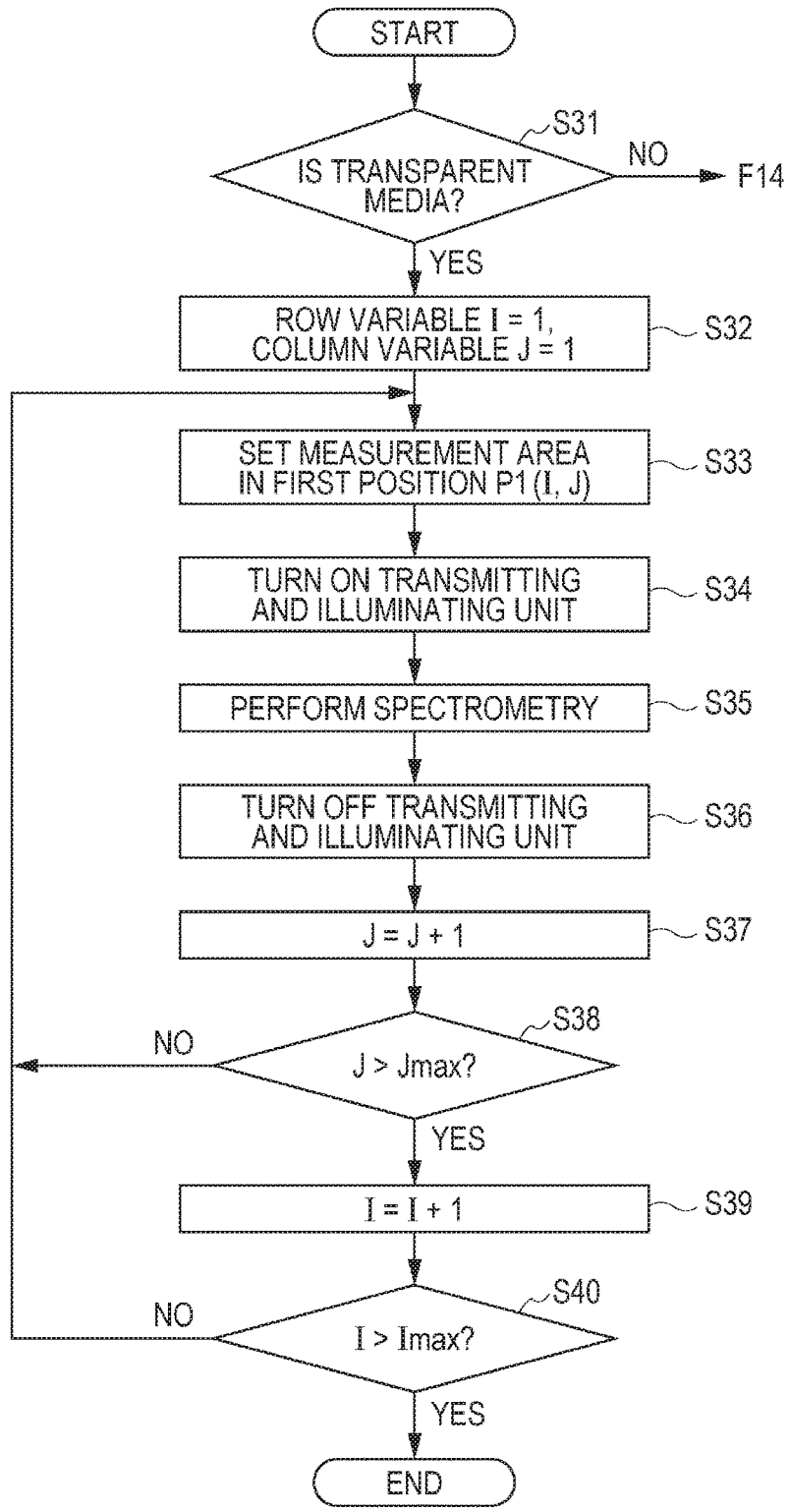
FIG. 13 is a flowchart illustrating an example of the correction pattern measurement processing of the first embodiment.
Figure 14:
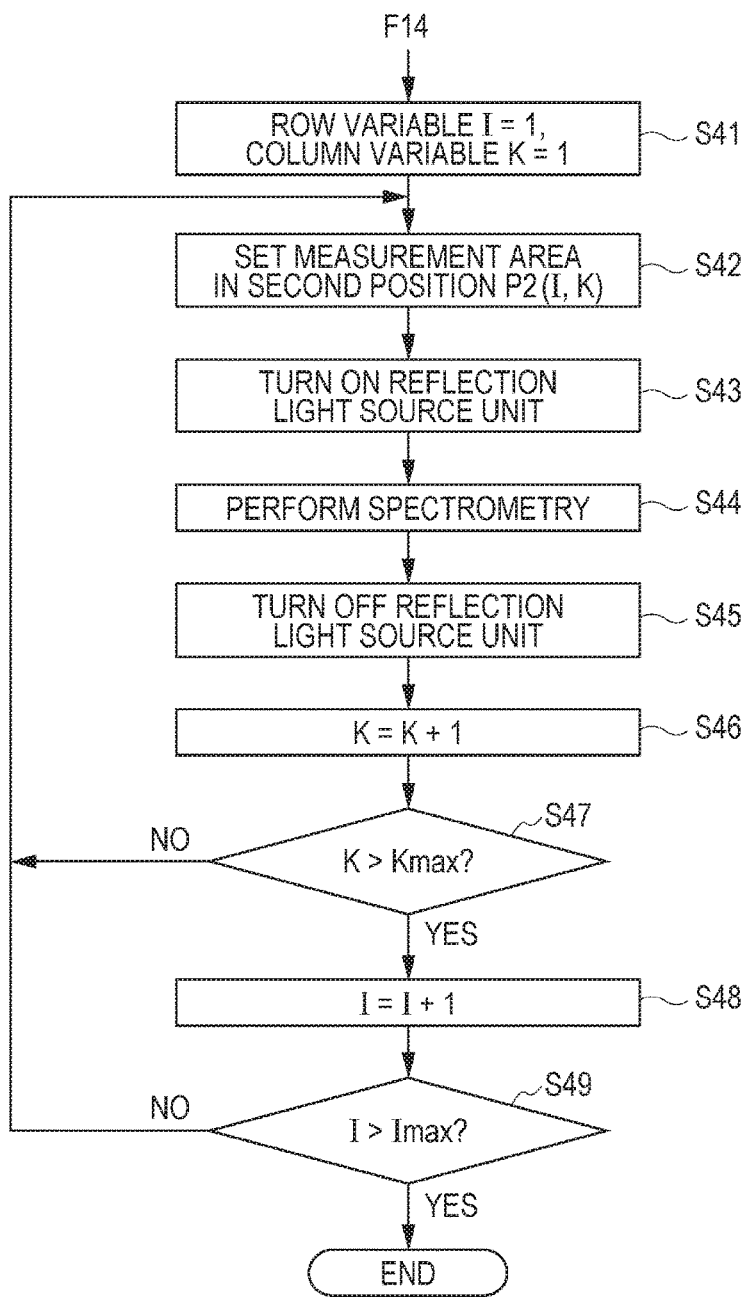
FIG. 14 is a flowchart illustrating another example of the correction pattern measurement processing of the first embodiment.

FIG. 8 is a flowchart illustrating an example of the print processing in the printer 1. FIG. 9 is a flowchart illustrating an example of media determination processing. FIG. 10 is a flowchart illustrating an example of correction pattern printing processing, and FIG. 11 and FIG. 12 are diagrams illustrating an example of the correction pattern in accordance with the media type. FIG. 13 and FIG. 14 are flowcharts illustrating an example of the correction pattern measurement processing.

In the print processing by the printer 1 of the example, first, the media determination processing which determines whether the type of the media A is the transparent media or the opaque media is conducted. The printer 1 prints the correction pattern including a plurality of color measurement patches by the printing unit based on the determination result of the media type, conducts color measurement processing on the plurality of printed color measurement patches, and calculates the color correction parameter based on the color measurement result. The printer 1 prints the image in accordance with the image data corrected using the color correction parameter.

In a case where the type of the media is known, the media determination processing may be omitted. The color correction parameter may be stored in the memory 153 after the color correction parameter is calculated and the print processing may be ended without conducting printing of the image data.

As illustrated in FIG. 8, in the print processing of the example, when the printer 1 receives instruction to conduct the print processing through an input by a user or from the external apparatus 20, the scanning control unit 154A controls the transport unit 12 to transport the media A along the Y-direction and sets the media A such that an area A where the image is not formed on the media A overlaps a scanning line of the spectrometer 17 (Step S1). In an initial state, the carriage 13 is regarded as being positioned in a home position.

Media Determination Processing

Next, the printer 1 conducts media determination processing which determines the type of the media A (Step S2). In the media determination processing of the example, it is determined whether the type of the media A is the transparent media or the opaque media based on a ratio of the light quantity in a case where illumination is made from the rear surface A2 by the transmitting and illuminating unit 18 and in a case where the illumination is not made.

Specifically, in the media determination processing, as illustrated in FIG. 9, first, the spectrometer 17 is moved by the scanning control unit 154A such that the measurement area Ar3 becomes the first measurement position Sc1 (see FIG. 5) including the rear front surface side illumination area Ar1 and sets the spectrometer 17 in the first measurement position Sc1 (Step S11).

When the measurement area Ar3 of the spectrometer 17 is set in the first measurement position Sc1, the light source 181 of the transmitting and illuminating unit 18 is turned on and the spectrometer 17 is set in a position at which the quantity of received light by the light receiving unit 172B becomes the maximum, and thereafter, Step S1 may be conducted to set the media A. With this, it is possible to easily and certainly move the spectrometer 17 to an appropriate position.

Next, the measurement control unit 154C controls the transmitting and illuminating unit 18 and turns off the light source 181 of the transmitting and illuminating unit 18 (Step S12). In a case where, the light source 181 is not turned on before Step S12 is conducted, Step S12 may be omitted.

After turning off the light source 181 of the transmitting and illuminating unit 18, the measurement control unit 154C drives the wavelength variable interference filter 5, sets a predetermined wavelength to the transmission parameter, and measures the quantity of received light of the light receiving unit 172B (in the following, referred to also as light quantity of turning-off period) Y1 (Step S13). The predetermined wavelength is, for example, any wavelength that falls within the visible light region.

The light quantity of turning-off period Y1 is, for example, the light quantity of external light reflected on the media surface A1 and received in the light receiving unit 172B or the like, and in a case where a measurement environment, for example, an installation site of the printer 1 is not changed, the light quantity of turning-off period Y1 is a value in accordance with reflectance of the media surface A1 of the media A.

Next, the measurement control unit 154C controls the transmitting and illuminating unit 18 and turns on the light source 181 of the transmitting and illuminating unit 18 (Step S14).

After turning on the light source 181 of the transmitting and illuminating unit 18, the measurement control unit 154C drives the wavelength variable interference filter 5, sets a predetermined wavelength to the transmission parameter, and measures the quantity of received light of the light receiving unit 172B (in the following, referred to also as light quantity of turning-on period) Y2 (Step S15).

The light quantity of turning-on period Y2 includes a light quantity of a portion of light transmitted through the media A of light, which is emitted from the transmitting and illuminating unit 18 and transmitted through the light transmitting unit 123 and with which the rear surface A2 is irradiated, other than the light quantity of the external light or the like included in the light quantity of turning-off period Y1.

As the predetermined wavelength, a wavelength which falls within a wavelength band and has a relatively large light quantity of the wavelengths included in light emitted from the light source 181 is set such that the detection amount of the quantity of transmitted light may be increased.

Next, the media determination unit 154D determines the type of the media A based on the light quantity of turning-off period Y1 and the light quantity of turning-on period Y2 (Step S16). For example, the media determination unit 154D, based on the following expression (5), determines that the type of the media A is the transparent media in a case where a ratio (Y2/Y1) of the light quantity of turning-on period Y2 to the light quantity of turning-off period Y1 is greater than a media determination threshold T1 and that the type of the media A is the opaque media in a case where the ratio is less than the threshold T1, and stores the determination result in the memory 153.

$$Y2/Y1 > T1 \quad (5)$$

Here, the light quantity of turning-on period Y2 depends on translucency of the media A, becomes larger in a case where translucency of the media A is high, and becomes smaller in a case where translucency of the media A is low. Accordingly, a value of the ratio Y2/Y1 becomes approximately 1 in a case where the media A is the opaque media which does not have translucency, and the value becomes a value larger than 1 in a case where the media A the transparent media having translucency. In the first embodiment, for example, it is set in such a way that media of which the transmittance of visible light (for example, transmittance of light having a wavelength of 550 nm) as the threshold T1 exceeds a predetermined value (for example, 90%) is able to be determined as the transparent media and media of which the transmittance of visible light is less than or equal to the predetermined value is able to be determined as the opaque media. The threshold T1, for example, is able to be obtained by setting the transparent media having a known transmittance to thereby measure the light quantity of turning-off period Y1 and the light quantity of turning-on period Y2 in an installation environment of the printer 1.

In Steps S13 and S15, the light quantity of turning-off period Y1 and the light quantity of turning-on period Y2 regarding a plurality of wavelengths may be measured and the media determination may be conducted based on an average value of the ratios (Y2/Y1) of the light quantity of turning-on period Y2 to the light quantity of turning-off period Y1 in the respective wavelengths. With this, the media type may be determined more accurately even in a case where wavelength dependency exists in the transmittance of the media A.

The media type determination method is not limited to the method described above and for example, as represented in the following expression (6), a method for determining the type based on the transmittance of media which is set may also be adopted. That is, the measurement area Ar3 of the spectrometer 17 is set in the first measurement position Sc1, the transmitting and illuminating unit 18 is turned on, and the light quantity (in the following, reference light quantity Y0) of the light receiving unit 172B obtained without setting the media A is acquired in advance, and in a case where a ratio of a difference value between the light quantity of turning-off period Y1 and the light quantity of turning-on period Y2 to the reference light quantity Y0, that is, the transmittance exceeds a second threshold T2 (for example, 0.9), it may also be determined that the type is the transparent media. In such a method, in a case where the light quantity from the transmitting and illuminating unit 18 is significantly greater than the light quantity of external light or the like, the reference light quantity Y0 may be regarded as the light quantity of light from the transmitting and illuminating unit 18, and the type of the media A may be easily determined with high accuracy based on the calculated transmittance value.

$$(Y2-Y1)/Y0 > T2 \quad (6)$$

Correction Pattern Printing Processing

Next, as illustrated in FIG. 8, the printer 1 conducts correction pattern printing processing (Step S3). In the correction pattern printing processing, the printer 1 forms a correction pattern (see FIG. 9 and FIG. 10) on the media A in accordance with the media type.

As illustrated in FIG. 10, the printing control unit 154B determines whether the media A is the transparent media or not based on the determination result of the media type stored in the memory 153 (Step S21).

In a case where the media A is the transparent media (Step S21: YES), the printing control unit 154B reads print data of the first correction pattern 31 for the transparent media illustrated in FIG. 11 as the correction pattern, and prints the first correction pattern 31 on the media A in synchronization with control by the scanning control unit 154A (Step S22).

On the other hand, in a case where the media A is the opaque media (Step S21: NO), the printing control unit 154B reads print data of the second correction pattern 32 for the opaque media illustrated in FIG. 12 and prints the second correction pattern 32 on the media A in synchronization with control by the scanning control unit 154A (Step S23).

That is, the carriage 13 is scanned by the scanning control unit 154A in the +X side, for example, at a constant speed. The printing control unit 154B specifies a position of the printing unit 16 of the carriage 13, for example, according to time elapsed from start of scanning and causes a nozzle for a predetermined color to eject an amount of ink in accordance with respective gradation values on a predetermined position based on the print data to thereby form an image (image formation operation). When the carriage 13 is moved to an end portion of the +X side, the scanning control unit 154A controls the supply unit 11 and the transport unit 12 to transport the media A in the +Y-direction (transport operation). The scanning control unit 154A scans the carriage 13 in the −X-direction and the printing control unit 154B forms an image having a color and a gradation value based on the print data.

The image formation operation and the transport operation described above are repeated and thus, the correction pattern is formed on the media A. As described above, the correction pattern is printed on the media A and the correction pattern printing processing is ended.

The first correction pattern 31, as illustrated in FIG. 11, is configured in such a way that a plurality of color measurement patches 30 are disposed in the X-direction and the Y-direction in a matrix shape. Each color measurement patch 30 has a rectangular shape in plan view when viewed from the Z-direction and the dimension of each side is greater than that of the rear front surface side illumination area Ar1 (light transmitting unit 123), the front surface side illumination area Ar2, and the measurement area Ar3 and in the first embodiment, the dimension in the X-direction is equal to the arranging pitch transported along the Y-direction, each color measurement patch 30 is disposed at a position in which any of the light transmitting units 123 is included. That is, in the first correction pattern 31, each color measurement patch 30 is disposed at a first position P1(I,J) in which the rear front surface side illumination area Ar1 described above is included. A row direction on the media A is set as the X-direction, a column direction on the media A is set as the Y-direction, and the row variable and the column variable are respectively set as I and J, and a position of each color measurement patch 30 is set as P1(I,J) in the first correction pattern 31.

Here, in the first embodiment, although the first correction pattern 31 in which the color measurement patches are disposed in a matrix shape of three row by six columns is illustrated, the number of rows and number of columns of the color measurement patches 30 is not limited thereto and a correction pattern including color measurement patches having any number of rows and number of columns may be formed.

The second correction pattern 32, as illustrated in FIG. 12, is configured in such a way that the plurality of color measurement patches 30 are disposed in a matrix shape. In the second correction pattern 32, respective color measurement patches 30 are disposed at a position displaced by a half pitch (p/2) of the arranging pitch p of the light transmitting unit 123 along the X-direction compared to the first correction pattern 31. That is, when the media A is transported along the Y-direction, respective color measurement patches 30 are disposed at a second position P2(I,K) which includes at least an area, which does not overlap the rear front surface side illumination area Ar1 between the light transmitting units 123, in the X-direction. I is a row variable and K is a column variable.

Correction Pattern Measurement Processing

Next, as illustrated in FIG. 8, the printer 1 conducts correction pattern measurement processing (Step S4). In the correction pattern measurement processing, the printer 1 turns on the transmitting and illuminating unit 18 or the reflection light source unit 171 with respect to the media A according to the media type and conducts spectrometry of each color measurement patch.

As illustrated in FIG. 13, the measurement control unit 154C determines whether the media A is the transparent media or not based on the determination result of the media type stored in the memory 153 (Step S31).

In a case where the media A is the transparent media (Step S31: YES), the measurement control unit 154C initializes the row variable I and the column variable J (Step S32).

Next, in order to conduct spectrometry of the color measurement patch 30 positioned on the first position P1(I, J), the scanning control unit 154A controls the transport unit 12 to transport the media A, controls the carriage moving unit 14 to move the spectrometer 17, and sets the measurement area Ar3 in the first position P1(I,J) (Step S33).

That is, the scanning control unit 154A controls the transport unit 12 and transports the media A until the color measurement patch 30 of the I-th row is positioned on the scanning line of the spectrometer 17. The scanning control unit 154A controls the carriage moving unit 14 to move the spectrometer 17 in the X-direction and sets the measurement area Ar3 in the first measurement position Sc1 which includes the rear front surface side illumination area Ar1 of the light transmitting unit 123 corresponding to the first position P1(I,J) (see FIG. 11).

Next, the measurement control unit 154C turns on the transmitting and illuminating unit 18 and irradiates the media A with light from the rear surface A2 side (Step S34). In this case, the media A is the transparent media and thus, light emitted from the rear surface A2 side and applied to the media A is transmitted to the spectrometer 17 side.

The measurement control unit 154C controls the measuring unit 172 to conduct spectrometry of transmitted light transmitted through the media A and the color measurement patch 30 (Step S35).

In the spectrometry, the measurement control unit 154C sequentially switches the driving voltage to the electrostatic actuator 56 of the wavelength variable interference filter 5 and measures value with respect to measurement wavelengths in 16 bands disposed to be spaced at 20 nm intervals in the visible light region of a wavelength ranging from 400 nm to 700 nm based on V-λ data stored in the memory 153. The obtained measured value is appropriately stored in the memory 153.

When spectrometry is ended, the measurement control unit 154C turns off the transmitting and illuminating unit 18 (Step S36).

Next, 1 is added to the column variable J (Step S37) and it is determined whether the column variable J exceeds the maximum value Jmax (Step S38).

In a case where the column variable J does not exceed the maximum value Jmax (Step S38: NO), spectrometry is not conducted for all color measurement patches 30 disposed in the I-th row and thus, the measurement control unit 154C conducts subsequent processing from Step S33.

On the other hand, in a case where spectrometry for all color measurement patches 30 disposed in the I-th row is ended and the column variable J exceeds the maximum value (Step S38: YES), the measurement control unit 154C adds 1 to the row variable I (Step S39), and determines whether the row variable I exceeds the maximum value Imax or not (Step S40).

In a case where the row variable I does not exceed the maximum value Imax (Step S40: NO), the color measurement patch 30 disposed in a row, for which spectrometry is not conducted, exists and thus, the measurement control unit 154C conducts subsequent processing from Step S33.

On the other hand, in a case where the row variable I exceeds the maximum value Imax (Step S40: YES), spectrometry is conducted for all color measurement patches and thus, the measurement control unit 154C ends the correction pattern measurement processing.

In a case where the determination result in Step S31 is "NO", that is, in a case where the media A is determined as not the transparent media, that is, in a case where the media A is the opaque media, spectrometry of) the second correction pattern 32 printed on the media A is conducted.

First, as illustrated in FIG. 14, the measurement control unit 154C initializes the row variable I and the column variable K (Step S41).

Next, in order to conduct spectrometry of the color measurement patch 30 positioned at the second position P2(I,K), the scanning control unit 154A, similar to Step S32, controls the transport unit 12 to transport the media A, controls the carriage moving unit 14 to move the spectrometer 17, and sets the measurement area Ar3 of the spectrometer 17 in the second position P2(I,K) (Step S42). That is, the scanning control unit 154A sets the measurement area Ar3 in the second measurement position Sc2 corresponding to the second position P2(I,K) (see FIG. 12).

Next, the measurement control unit 154C turns on the reflection light source unit 171 and irradiates the front surface side illumination area Ar2 of the media surface A1 with light (Step S43). In this case, light reflected by the media surface A1 of the media A is measured by the spectrometer 17. A backing surface 122B is disposed at the rear surface A2 side of the media A. Even in a case where light, which is transmitted through the media A, is reflected by the backing surface 122B, and then is transmitted through the media A again to be incident on the spectrometer 17, exists, the backing surface 122B is made white and has substantially no wavelength dependency of reflectance and thus, reduction in the measurement accuracy may be suppressed.

Next, the measurement control unit 154C controls the measuring unit 172 similar to Step S34 to conduct spectrometry of reflected light in the media surface A1 to thereby conduct spectrometry of the color measurement patch 30 (Step S44).

When spectrometry is ended, the measurement control unit 154C turns off the reflection light source unit 171 (Step S45).

Next, 1 is added to the column variable K (Step S46) and it is determined whether the column variable K exceeds the maximum value Kmax or not (Step S47).

In a case where the column variable K does not exceed the maximum value Jmax (Step S47: NO), spectrometry is not conducted for all color measurement patches 30 disposed in the I-th row and thus, the correction pattern measurement processing returns to Step S42.

On the other hand, in a case where spectrometry for all color measurement patches 30 disposed in the I-th row is ended and the column variable K exceeds the maximum value (Step S47: YES), the measurement control unit 154C adds 1 to the row variable I (Step S48), and determines whether the row variable I exceeds the maximum value Imax or not (Step S49).

In a case where the row variable I does not exceed the maximum value Imax (Step S49: NO), a row for which spectrometry is not conducted exists and thus, the measurement control unit 154C conducts subsequent processing from Step S42.

On the other hand, in a case where the row variable I exceeds the maximum value Imax (Step S49: YES), spectrometry is conducted for all color measurement patches and thus, the measurement control unit 154C ends the correction pattern measurement processing.

Calculation of Color Correction Parameter

Next, as illustrated in FIG. 8, the color correction parameter calculation 154F calculates the color correction parameter based on the spectrometry result in the correction pattern measurement processing of Step S4 and stores the color correction parameter in the memory 153 (Step S5).

In Step S5, first, the color measurement operation unit 154E calculates a color measurement value of each color measurement patch 30 of the correction pattern based on the measurement result acquired in the correction pattern measurement processing of Step S4. The color correction parameter calculation 154F calculates the color correction parameter based on the color measurement value of each color measurement patch 30.

The color correction parameter is a parameter for converting recording density of inks corresponding to each color of the image data for printing into an adequacy value in accordance with the observation condition in order to obtain desired color reproducibility. The color correction parameter may include conversion parameters used for various conversion processing, for example, a conversion parameter used when performing the color coordinate conversion of converting the image data for printing, which is the RGB data, to the CMYK data and a conversion parameter used when performing the halftone processing of converting the image data after the color coordinate conversion to the print data corresponding to the recording density of ink droplets. Also, the color correction parameter used for correction image data for printing (RGB data) before the color coordinate conversion, the image data for printing (CMYK data) after the color coordinate conversion, the correction parameter correcting the print data or the like may be included as an example.

A known method described in JP-A-2007-43488 or the like may be used as the color correction parameter calculation method. For example, in the apparatus described in JP-A-2007-43488, a color correction LUT (color correction parameter) used during the color coordinate conversion is calculated using the color measurement value of the color correction pattern. That is, the color correction pattern is printed using an initial LUT in which the RGB lattice point is correlated with the ink ejection amount and a color correction LUT is calculated based on the color measurement value of the color correction pattern and the initial LUT.

Print Processing

The color correction parameter described above is used for correcting colors of the image in accordance with image data during the print processing by the printing unit 16.

In the print processing on the media A by the printer 1, as illustrated in FIG. 8, the printer 1 acquires the image data for printing from the external apparatus 20 or the like (Step S6).

Next, the printing control unit 154B performs color correction of the image data for printing using the color correction parameter and generates corrected image data (Step S7). A known method described in JP-A-2007-43488 or the like may be used as the color correction method. For example, as described above, the color coordinate conversion of the image data for printing is performed using the color correction LUT calculated based on the color measurement value of the color correction pattern and the initial LUT.

As described above the color correction parameter may be a parameter for correcting the image data which is the CMYK data. In this case, after the color conversion processing of the image data which is the RGB data is conducted, the image data (CMYK data) is corrected using the color correction parameter. The color correction parameter may be a parameter correcting the print data after the halftone processing. In this case, the print data is corrected using the color correction parameter.

The printing control unit 154B conducts the halftone processing on the corrected image data to generate the print data and prints an image on the media A in synchronization with control by the scanning control unit 154A (Step S8). The print data is corrected using the color correction parameter in accordance with the media type and thus, an image having a color in accordance with the observation condition is printed.

The printing control unit 154B determines whether it is intended to continue printing or not (Step S9). In a case where the determination result is "YES", the process returns to Step S6 and the print processing for other image data for printing is conducted. On the other hand, in a case where the determination result is "NO", the print processing is ended.

Effect of First Embodiment

In the first embodiment, the spectrometer 17 is able to move along the X-direction with respect to the media A and the platen 122. The platen 122 includes a plurality of light transmitting units 123 along the X-direction. In such a configuration, even when the media A is the transparent media, spectrometry is able to be conducted in a state where the rear surface A2 is irradiated with light transmitted through the light transmitting unit 123. For that reason, the transparent media has translucency and thus, even in a case where spectrometry of the transparent media in which a color of an image is changed according to the presence/absence of transmitted light transmitted from the rear surface A2 side to the media surface A1 side, that is, the observation condition, is conducted, spectrometry is able to be conducted under the measurement condition according to the observation condition, and the color of the image is able to be measured with high accuracy.

In the first embodiment, the spectrometer 17 is mounted on the carriage 13, the transport unit 12 transporting the media A in the Y-direction is provided, and the plurality of light transmitting units 123 are disposed on the scanning line of the spectrometer 17 along the X-direction. In such a configuration, the spectrometer 17 is moved along the X-direction to thereby make it possible to conduct spectrometry in a plurality of sites of a plurality of first measurement positions Sc1 and a plurality of second measurement positions Sc2.

The media A is transported in the Y-direction to thereby make it possible to change the measurement position even in the Y-direction and change the measurement position two dimensionally in the media surface A1. Accordingly, it is possible to improve the use efficiency of the media and prevent increase in running costs by more than that in a configuration in which only a single light transmitting unit 123 is provided and the media A is transported to thereby make it possible to move the measurement position only along the Y-direction.

In the configuration in which only a single light transmitting unit 123 is provided, a configuration in which the platen 122 or the light transmitting unit 123 and the spectrometer are simultaneously moved in order to achieve improvement of the use efficiency of the media may be adopted. However, in this case, when the configuration in which the platen 122 or the light transmitting unit 123 is moved, the number of components is increased and thus, there is a risk that manufacturing cost is increased and the apparatus becomes larger. In contrast, in the first embodiment, it is possible to change the measurement position two dimensionally even without moving the platen 122 or the light transmitting unit 123 and measure the plurality of color measurement patches 30 with a more simple configuration.

In the first embodiment, the spectrometer 17 is moved along the X-direction to thereby make it possible to conduct spectrometry in a plurality of sites of a plurality of first measurement positions Sc1 and a plurality of second measurement positions Sc2 and change the measurement condition. With this, it is possible to conduct spectrometry under the measurement condition in accordance with the type of the media A (transmissivity) or the observation condition to acquire the color measurement result and achieve improvement of color reproducibility of an image based on the color measurement result.

In the first embodiment, the reflection light source unit 171 is provided and thus, it is possible to irradiate the media surface A1 with light having a desired light quantity. Accordingly, the measurement accuracy may be improved when the opaque media is measured.

The first embodiment is provided with the transmitting and illuminating unit 18 and is configured in such a way that light emitted from the transmitting and illuminating unit 18 is transmitted through the light transmitting unit 123 and is incident onto the rear surface A2. In such a configuration, it is possible to irradiate the rear surface A2 of the media A with light having a desired light quantity from the light transmitting unit 123. Accordingly, the measurement accuracy may be improved when the transparent media is measured. It is possible to make the light quantities of transmitted light uniform in each of the plurality of light transmitting units 123. In particular, even when the observation condition corresponds to a case where light is emitted from the rear surface A2 side of the transparent media using backlight and the formed image is displayed, the color of the image may be measured with high accuracy.

In the first embodiment, the platen 122 is a plate-shaped member and the light transmitting unit 123 includes the light-transmitting hole 123A penetrating through the platen 122 and the light quantity uniform optical member 123B disposed within the light-transmitting hole 123A. In such a configuration, the rear surface A2 of the media A may be maintained by the holding surface 122A of the plate-shaped is platen 122 and flatness of the media surface A1 and the rear surface A2 of the media A is easily maintained during spectrometry. It is possible to make light incident onto the rear surface A2 while maintaining the flatness. It is possible to achieve improvement in the measurement accuracy of spectrometry.

In the first embodiment, the light quantity uniform optical member 123B is provided in the light transmitting unit 123. For that reason, is possible to make uniform light incident onto the rear surface A2 of the media A from the light transmitting unit 123 and improve the color measurement accuracy when the transparent media is measured.

The backing surface 122B, in which the light transmitting unit 123 is not provide, of the holding surface 122A of the platen 122 is made white or black. In such a configuration, when spectrometry is conducted using the backing surface 122B as a background, that is, spectrometry is conducted in the second measurement position Sc2, it is possible to prevent reduction in the measurement accuracy. For example, even in a case where light transmitted through the media A and reflected by the backing surface 122B is transmitted through the media A again, the backing surface 122B is made white of which reflectance is substantially uniform between a plurality of wavelengths in the visible light to thereby make it possible to prevent the light quantity of light reflected on the backing surface 122B from being changed according to the wavelength. The backing surface 122B is made black to thereby make it possible to prevent light from being reflected on the backing surface 122B. As described above, it is possible to prevent reduction of the measurement accuracy by the reflected light reflected on the backing surface 122B.

In the first embodiment, it is determined whether the media type is the transparent media or the opaque media based on a ratio of the light quantity of turning-off period Y1 measured in a state where the transmitting and illuminating unit 18 is turned off and the light quantity of turning-on period Y2 measured in a state where the transmitting and illuminating unit 18 is turned on (see the expression (5)). As such, the measured value of the transmitted light is used when the transmitting and illuminating unit 18 is turned on to thereby make it possible to easily determine the media type. As illustrated in the expression (5), the media type is determined based on the ratio of the light quantity of turning-off period Y1 and the light quantity of turning-on period Y2 to thereby make it possible to prevent an erroneous determination due to influence by external light or the like and determine the media type more accurately.

In the first embodiment, in a case where the media type is the transparent media, the first correction pattern in which the color measurement patch 30 is disposed in the first position P1(I,J) which overlaps the light transmitting unit 123 is printed and in a case where the media type is the opaque media, the second correction pattern 32 in which the color measurement patch 30 is disposed in the second position P2(I,K) which at least overlaps the backing surface 122B between the light transmitting units 123 is printed. Spectrometry of the correction patterns 31 and 32 are conducted to thereby make it possible to conduct spectrometry in accordance with the media type and the observation condition.

In the first embodiment, it is possible to calculate the color measurement value from the results of spectrometry of the correction patterns 31 and 32, calculate the color correction parameter using the color measurement value, and perform the color correction of the image data. It is possible to perform the color correction according to the media type and the observation condition to change the printing condition, and improve color reproducibility of an image.

In the first embodiment, the printing unit 16 and the spectrometer 17 are mounted on a single carriage 13 to thereby make it possible to achieve simplification and miniaturization of an apparatus. A distance between the printing unit 16 and the spectrometer 17 is not changed and thus, it is possible to control respective positions of the printing unit 16 and the spectrometer 17 using the same coordinate system. With this, it is possible to further prevent processing load due to control of the position by more than that in a configuration in which the position is controlled based on different coordinate systems for the printing unit 16 and the spectrometer 17 when the image printed by the printing unit 16 is measured using the spectrometer 17.

Second Embodiment

Next, a second embodiment according to the invention will be described.

In the first embodiment, the configuration in which a plurality of the light transmitting units 123, each of which includes the light-transmitting hole 123A and the light quantity uniform optical member 123B, are provided in the plate-shaped platen 122 is illustrated. In contrast, the second embodiment is different from the first embodiment in that the platen is configured to include a plurality of plate-shaped members and light is transmitted to the rear surface A2 side of the media A from gaps formed between plate-shaped portions as the light transmitting unit.

In the following description, the same configurations and processing as those of the first embodiment are denoted by the same reference numerals and descriptions thereof will be omitted or simplified.

Figure 15:
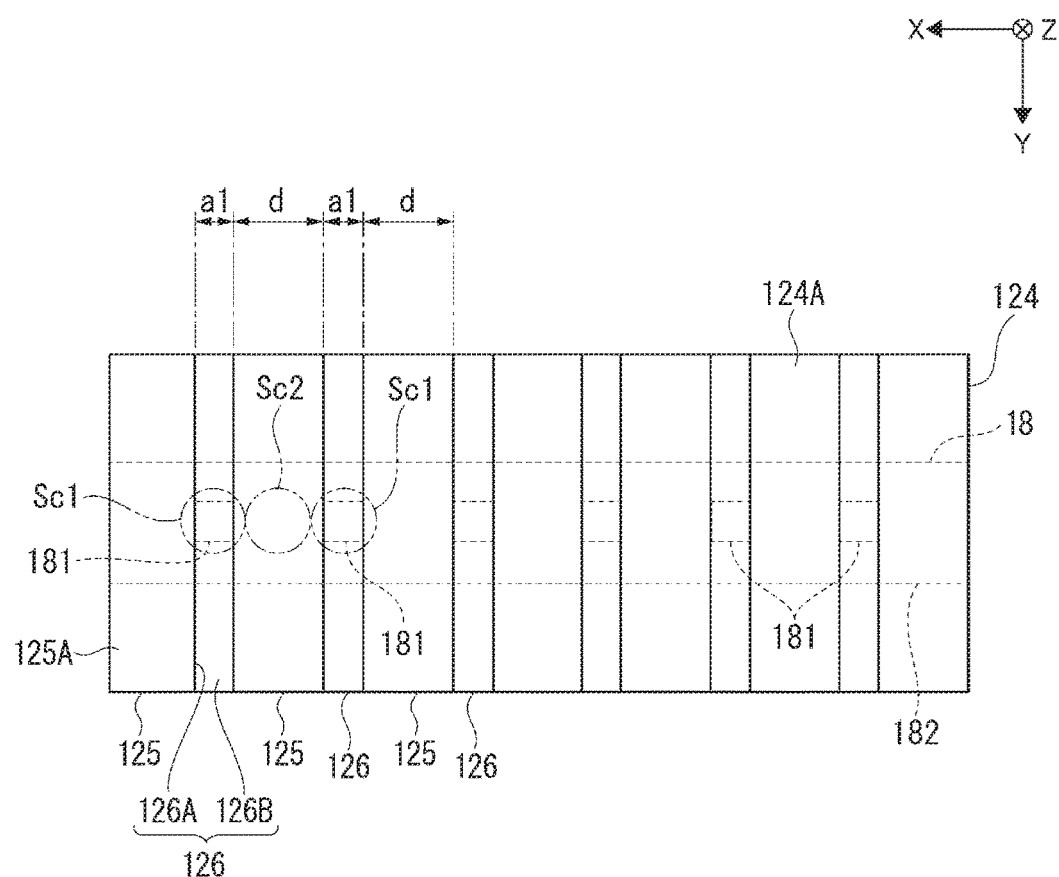
FIG. 15 is a plan view illustrating a schematic configuration of a platen of a second embodiment.

FIG. 15 is a plan view illustrating a schematic configuration of the platen 124 of the second embodiment.

The platen 124 includes a plurality of plate-shaped members 125 and a plurality of light transmitting units 126 and similar to the first embodiment, the platen abuts the rear surface A2 of the media A in the holding surface 124A which is the surface of the −Z side and holds the media A. The platen 124 is configured in such a way that light emitted from the transmitting and illuminating unit 18 is able to be transmitted in the −Z direction by the light transmitting unit 126.

The plate-shaped member 125 is a rectangular member in plan view when viewed from the Z direction. The surface 125A of the −Z side (backing surface 125A) of the plate-shaped member 125 is made white or black. The second measurement position Sc2 is set in the backing surface 125A of the plate-shaped member 125, the color measurement patch is disposed in the backing surface 125A (see FIG. 12) during spectrometry of the opaque media similar to the first embodiment, and the backing surface 125A functions as background. The dimension in the X-direction of the plate-shaped member 125 is d. A plurality of plate-shaped members 125 are disposed to be spaced apart from each other by dimension of a1 along the X-direction and the light transmitting unit 126 is provided between the plurality of plate-shaped members 125.

The light transmitting unit 126 is provided between the plate-shaped members 125 and has a rectangular appearance in plan view when viewed from the Z direction. The light transmitting unit 126 includes gaps 126A each of which has dimension of a1 in the X-direction and the light quantity uniform optical members 126B disposed in the gaps 126A. In the +Z side of the light transmitting unit 126, the light source 181 of the transmitting and illuminating unit 18 is disposed.

For example, a diffusion plate may be used as the light quantity uniform optical member 126B. With this, it is possible to cause light, of which the light quantity distribution in the XY plane is uniform and is emitted from the light source 181, to be transmitted to the rear surface A2 side. The first measurement position Sc1 is set to be overlapped with the light transmitting unit 126 and the light source 181 and similar to the first embodiment, the color measurement patch 30 (see FIG. 11) is disposed during spectrometry of the transparent media.

Effect of Second Embodiment

The platen 124 includes a plurality of plate-shaped members 125 and a plurality of light transmitting units 126 provided in the gaps between the plurality of the plate-shaped members 125, and is a member having a plate shape in its entirety. In such a configuration, it is possible to hold the rear surface A2 of the media A by the holding surface 124A of the platen 124 and flatness of the media surface A1 and the rear surface A2 of the media A is easily maintained during spectrometry. It is possible to make light incident onto the rear surface A2 while maintaining the flatness. It is possible to achieve improvement in the measurement accuracy of spectrometry.

In the second embodiment, the light quantity uniform optical member 126B is provided in the light transmitting unit 126. For that reason, it is possible to make uniform light incident onto the rear surface A2 of the media A from the light transmitting unit 123 and improve the color measurement accuracy when the transparent media is measured.

In a case where a rectangular diffusion plate is used as the light quantity uniform optical member 126B, the rectangular plate-shaped member 125 and the rectangular light quantity uniform optical member 126B are alternately arranged in the X-direction to thereby make it possible to easily form the platen 124.

Modification Example

The invention is not limited to the first and second embodiments described above and intends to include the configuration obtained through alterations and modifications to the embodiments or a combination of the embodiments in a scope for achieving aspects of the invention.

In the first and second embodiments, a configuration in which a determination whether the type of media is the transparent media or the opaque media is capable of being made is illustrated. However, based on the Expression (7) to be described below a configuration in which a determination whether the type of media is semi-transparent media is capable of being made maybe also be adopted. That is, in a case where the transmittance is less than or equal to the second threshold T2 and exceeds a third threshold T3 (for example, 0.5), the media determination unit 154D may determine the media as the semi-transparent media having transmittance lower than that of the transparent media and high translucency.

In a case where the media A is the semi-transparent media, both color correction parameters for the transparent media and the opaque media may be acquired as the color correction parameter which will be described later, the image data may be corrected using the appropriate color correction parameter, for example, the image data is corrected using the appropriate color correction parameter according to a state during observations and an image may be printed. That is, when the image printed in the media A is observed, the color correction parameter for transparent media may be used in a case where illumination is made from the rear surface A2 side and the color correction parameter for opaque media may be used in a case where illumination is not made. With this, it is possible to correct the image data using the appropriate color correction parameter according to the observation condition and improve color reproducibility.

$$T3<(Y2-Y1)/Y0 \leq T2 \quad (7)$$

Figure 16:
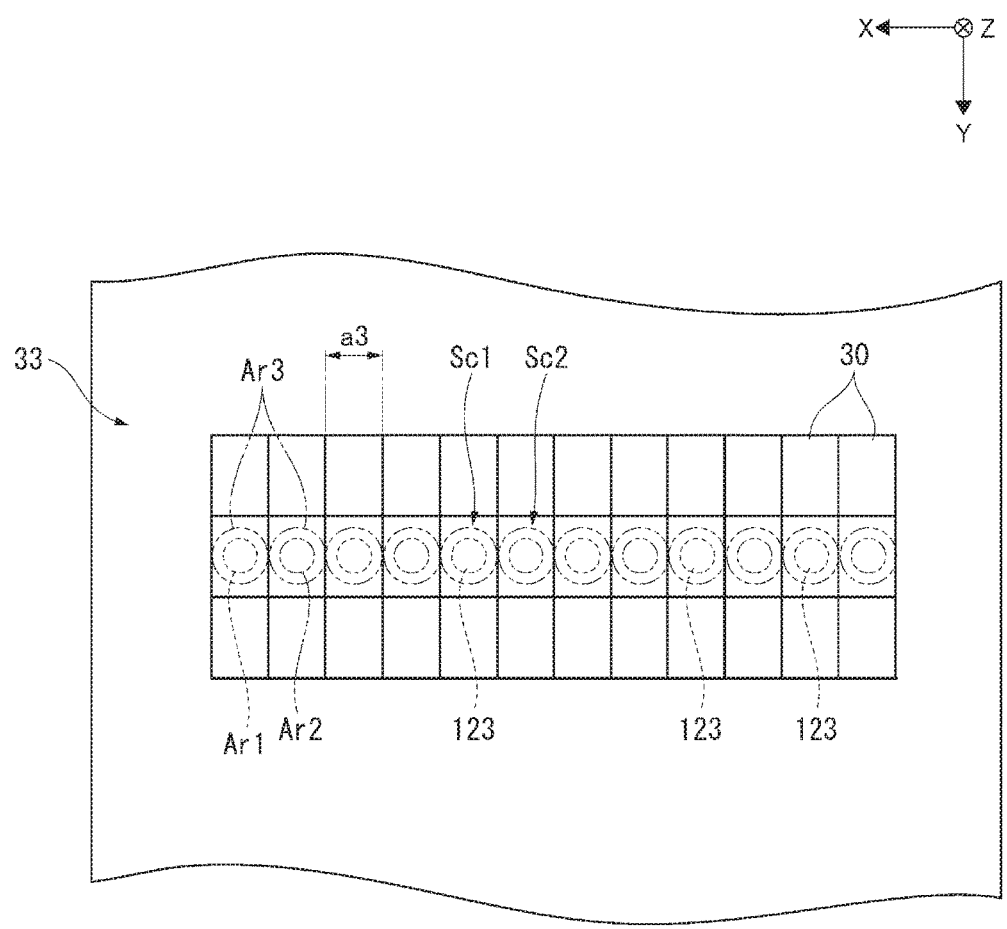
FIG. 16 is a diagram schematically illustrating a modification example of the correction pattern.

In the first and second embodiments, although the dimension of the color measurement patch 30 in the X-direction of is set to an arranging pitch p (twice the dimension a3 of measurement area Ar3), the invention is not limited thereto. For example, arbitrary dimension may be set as long as spectrometry in respective measurement positions Sc1 and Sc2 is capable of being conducted at a desired accuracy level. For example, in a case where the dimension a3 of the measurement area Ar3 is larger than diameters a1 and a2 of the rear front surface side illumination area Ar1 and the front surface side illumination area Ar2, as in the correction pattern 33 illustrated in FIG. 16, the dimension of the color measurement patch 30 in the X-direction which has the same dimension as the dimension a3 of the measurement area Ar3 may be used. The correction pattern 33 is used to thereby make it possible to increase filling rate of the color measurement patch 30 and further suppress consumption of the media A.

In the first and second embodiments, the configuration in which the measurement area Ar3 is set in the first measurement position Sc1 when spectrometry of the first correction pattern 31 formed in the transparent media is conducted, spectrometry of the transmitted light emitted from the transmitting and illuminating unit 18 is conducted, and the color correction parameter is calculated is illustrated. However, the invention is not limited thereto. For example, spectrometry of the reflected light may be conducted in the second measurement position Sc2 even regarding the transparent media and the color correction parameter may be calculated. That is, the correction pattern 33 illustrated in FIG. 16 may be printed in the transparent media and spectrometry of both the first measurement position Sc1 and the second measurement position Sc2 may be conducted when spectrometry of the correction pattern 33 is conducted. In this case, the measurement area Ar3 is set in the second measurement position Sc2, spectrometry of the light reflected from the media surface A1 is conducted and the color correction parameter is calculated in a state where the reflection light source unit 171 is turned on to thereby make it possible to calculate the color correction parameter capable of being appropriately used in the observation condition where light is not incident on the rear surface side of the transparent media.

In a case where the media type is the transparent media, the user is able to select the presence/absence of incident light onto the rear surface side of the transparent media as the observation condition to thereby make it possible to select the appropriate color correction parameter according to the presence/absence incident light and conduct the color correction in accordance with the observation condition.

In the first and second embodiments, although the configuration in which only the transmitting and illuminating unit 18 is turned on when the correction pattern formed in the transparent media is measured in the first measurement position Sc1 is illustrated, the invention is not limited thereto. For example, spectrometry may be conducted in a state where the reflection light source unit 171 is also turned on simultaneously. With this, it is possible to calculate the appropriate color correction parameter and conduct the appropriate color correction even for the observation condition (for example, in a case where an illumination device is installed in the rear surface side and light having high strength such as sunlight is incident on the media surface side, or the like) in which light is incident onto the transparent media from both surfaces.

In the first and second embodiments, although the dimension a3 of the measurement area Ar3 is set to be greater than the diameters a1 and a2 of the rear front surface side illumination area Ar1 and the front surface side illumination area Ar2, the invention is not limited thereto. For example, the dimension a3 may be set to be smaller than respective diameters a1 and a2. In such a configuration, it is possible to conduct spectrometry using the entire area of the measurement area Ar3 and increase the quantity of received light in the light receiving unit 172B.

In the first and second embodiments, although the configuration in which the transmitting and illuminating unit 18 is provided is illustrated, the invention is not limited thereto. A configuration in which the transmitting and illuminating unit 18 is not provided and external light incident on the light transmitting unit is transmitted to the rear surface A2 side may be adopted. With this, it is possible to achieve simplification of the configuration.

In the first and second embodiments described above, although the light transmitting unit includes the light quantity uniform optical member, the invention is not limited thereto. For example, in the first embodiment, the light transmitting unit 123 may be configured by only the light-transmitting hole 123A formed in the platen 122 and in the first embodiment, the light transmitting unit 126 may be configured by only the gap 126A formed in the plate-shaped member 125. With this, it is possible to achieve simplification of the configuration.

In the first and second embodiments described above, although the configuration in which the reflection light source unit 171 is provided is illustrated, the invention is not limited thereto and may adopt a configuration in which the reflection light source unit 171 is not provided.

In the first and second embodiments described above, although the configuration in which the spectrometer 17 and the printing unit 16 are mounted on the carriage 13, the invention is not limited thereto.

That is, the printer may be configured in such a way that a carriage for spectrometry on which the spectrometer 17 is mounted separately from the carriage for printing in which the printing unit 16 is provided and the carriage for image-capturing is able to be moved by the moving mechanism having the same configuration as the carriage moving unit 14 of the first and second embodiments. In such a configuration, a first directional movement unit for relatively moving the carriage for printing in the X-direction with respect to the medium and a second directional movement unit for relatively moving the carriage for printing in the Y-direction are separately provided.

In the first and second embodiment described above, although the configuration in which the carriage 13 is moved along the X-direction is illustrated, the invention is not limited thereto. For example, it may be configured in such a way that the spectrometer 17 and the media A are relatively movable and otherwise, the carriage 13 is fixed and the media A is moved with respect to the carriage 13. In this case, it is possible to prevent vibration of the wavelength variable interference filter 5 accompanied by the movement of the carriage 13 and stabilize the transmission parameter of the wavelength variable interference filter 5.

Furthermore, a specific structure when embodying the invention may be appropriately changed to other structures or the like within a range capable of achieving an advantage of some aspects of the invention.

The entire disclosure of Japanese Patent Application No. 2015-213409, filed Oct. 29, 2015 is expressly incorporated by reference herein.

What is claimed is:

1. A measuring device comprising:
    a spectrometer which is relatively movable between media having a first surface and a second surface which is opposite to the first surface; and
    a holding unit that is separate and apart from the spectrometer, the holding unit being configured to support the second surface of the media,
    wherein the holding unit includes a plurality of apertures that are configured to transmit light, and a plurality of plate-shaped members, and each of the apertures defines a gap between one of the plate-shaped members and another one of the plurality of plate-shaped members.

2. The measuring device according to claim 1, further comprising:
    a first light irradiation unit which irradiates the second surface side of the media with light through the apertures.

3. The measuring device according to claim 1, further comprising:
    a second light irradiation unit which irradiates the first surface side of the media with light.

4. The measuring device according to claim 1,
    wherein a surface of the holding unit that supports the second surface of the media is white or black.

5. The measuring device according to claim 1,
    wherein each aperture includes a light quantity uniform optical system configured to make a light quantity distribution of transmitted light uniform.

6. The measuring device according to claim 1, further comprising:
    a first light irradiation unit which irradiates the second surface side of the media with light,
    wherein a type of the media is determined based on a measurement result in the spectrometer when light is emitted from the first light irradiation unit.

7. The measuring device according to claim 1, further comprising:
    a carriage on which the spectrometer is mounted; and
    a moving mechanism which moves the carriage in one direction with respect to the media.

8. The measuring device according to claim 7,
    wherein the plurality of apertures are disposed along the one direction.

9. A printing apparatus comprising:
    a measuring device according to claim 1; and
    a printing unit which forms an image on the media.

10. The printing apparatus according to claim 9, further comprising:
    a carriage on which the spectrometer and the printing unit are mounted.

11. The printing apparatus according to claim 9,
    wherein in a case where the media is a transparent media, the printing unit forms color measurement patches on an area which overlaps any of the plurality of light transmitting units, and
    in a case where the media is an opaque media, the printing unit forms the color measurement patch on an area which does not overlap at least the light transmitting units.

12. The printing apparatus according to claim 9, further comprising:
    a parameter calculation unit which calculates a color correction parameter when an image is formed by the printing unit based on a result of the measurement by the spectrometer.

13. A printing apparatus comprising:
    a measuring device according to claim 2; and
    a printing unit which forms an image on the media.

14. A printing apparatus comprising:
    a measuring device according to claim 3; and
    a printing unit which forms an image on the media.

15. A printing apparatus comprising:
    a measuring device according to claim 4; and
    a printing unit which forms an image on the media.

16. A printing apparatus comprising:
    a measuring device according to claim 5; and
    a printing unit which forms an image on the media.

17. A measuring device comprising:
    a spectrometer including an interference filter having a fixed substrate and a movable substrate that each include a reflective film, the interference filter being movable relative to a media having a first surface and an opposite second surface; and
    a platen that is separate and apart from the interference filter, the platen being configured to support the second surface of the media,
    wherein the platen includes a plurality of apertures that are configured to transmit light.

* * * * *